United States Patent
Jelinek

(10) Patent No.: US 10,101,277 B2
(45) Date of Patent: Oct. 16, 2018

(54) POLY(METHYL METHACRYLATE)-SUPPORTED POLYDIACETYLENE FILMS AS COLORIMETRIC AND/OR FLUORESCENT DETECTORS

(71) Applicant: B.G. NEGEV TECHNOLOGIES & APPLICATIONS LTD. AT BEN-GURION UNIVERSITY, Beer-Sheva (IL)

(72) Inventor: Raz Jelinek, Reut (IL)

(73) Assignee: B.G. NEGEV TECHNOLOGIES & APPLICATIONS LTD. AT BEN-GURION UNIVERSITY, Beer-Sheva (IL)

( * ) Notice: Subject to any disclaimer, the term of this patent is extended or adjusted under 35 U.S.C. 154(b) by 0 days.

(21) Appl. No.: 14/795,261

(22) Filed: Jul. 9, 2015

(65) Prior Publication Data
US 2016/0041102 A1 Feb. 11, 2016

Related U.S. Application Data

(60) Provisional application No. 62/022,234, filed on Jul. 9, 2014.

(51) Int. Cl.
G01N 21/75 (2006.01)
G01N 21/76 (2006.01)
(Continued)

(52) U.S. Cl.
CPC ............. *G01N 21/76* (2013.01); *B05D 1/005* (2013.01); *B05D 3/067* (2013.01); *C08F 138/00* (2013.01);
(Continued)

(58) Field of Classification Search
CPC ........ G01N 21/75; G01N 21/76; G01N 21/00; G01N 2021/757
USPC ........................................... 422/425, 400, 50
See application file for complete search history.

(56) References Cited

U.S. PATENT DOCUMENTS

2002/0034475 A1 3/2002 Ribi
2008/0293095 A1 11/2008 Jelinek

FOREIGN PATENT DOCUMENTS

WO WO 99/10743 3/1999
WO WO 2014/052794 4/2014

OTHER PUBLICATIONS

Park, Moo-Kyung, Colorimetric Detection of Chelating Agents Using Polydiacetylene Vesicles, Korean Chem. Eng. Res., vol. 49, No. 3, Jun. 2011, pp. 348-351.*

(Continued)

*Primary Examiner* — Christine T Mui
(74) *Attorney, Agent, or Firm* — Nixon & Vanderhye P.C.

(57) ABSTRACT

Colorimetric and/or fluorescent detectors, which include a polydiacetylene (PDA) film deposited on a polymethylmetacrylate (PMMA) substrate. There are also colorimetric and/or fluorescent detectors which have a solid organic matrix comprising one or more PDAs deposited on the PMMA substrate, wherein the PDA includes polymerized units of one or more diacetylene monomers, and wherein the matrix further comprises at least one recognition element of an analyte. There are also methods for detecting analytes using this detector, uses thereof and a methods for its preparation.

15 Claims, 15 Drawing Sheets

(51) Int. Cl.
  *C08F 138/00* (2006.01)
  *G01N 33/52* (2006.01)
  *B05D 1/00* (2006.01)
  *B05D 3/06* (2006.01)
  *G01N 21/00* (2006.01)
  *G01N 31/22* (2006.01)

(52) U.S. Cl.
  CPC ........... *G01N 33/523* (2013.01); *G01N 31/22* (2013.01); *G01N 2021/757* (2013.01)

(56) References Cited

OTHER PUBLICATIONS

Park, Moo-Kyung, Colorimetric Detection of Chelating Agents Using Polydiacetylene Vesicles, English Machine Translation From Google Translate, Korean Chem. Eng. Res., vol. 49, No. 3, Jun. 2011, pp. 348-351.*

English Translation of Park, Moo-Kyong et al, Colorimetric Detection of Chelating Agents Using Polydiacetylene Vesicles, Aug. 2016, pp. 1-14.*

Pindzola et al, Antibody-functionalized polydiacetylene coatings on nanoporous membranes for microorganism detection, Chem. Commun., 2006, 906-908. (Year: 2006).*

Pindzola et al, Supplementary Material for Chemical Communications: Antibody-functionalized polydiacetylene coatings on nanoporous membranes for microorganism detection, Chem. Commun., 2006, 1-3 (Year: 2006).*

Kootery et al., "Poly(methyl methacrylate)-Supported Polydiacetylene Films: Unique Chromatic Transitions and Molecular Sensing", ACS, Mar. 2014, eight pages, pp. 8613-8620.

International Search Resort issued in PCT/IL2015/050717 dated Oct. 27, 2015, pp. 1-3.

* cited by examiner

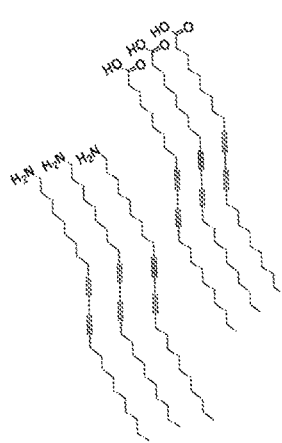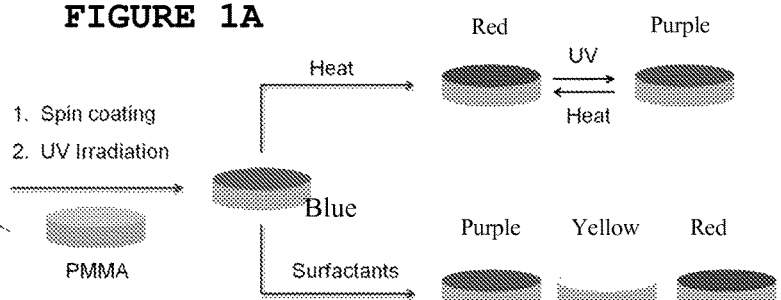
FIGURE 1A
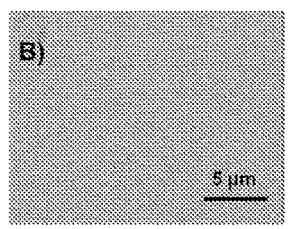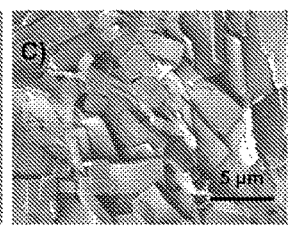
FIGURE 1B    FIGURE 1C

POLY(METHYL METHACRYLATE)-SUPPORTED POLYDIACETYLENE FILMS AS COLORIMETRIC AND/OR FLUORESCENT DETECTORS

This application claims priority to U.S. Provisional Application No. 62/022,234 filed Jul. 9, 2014, the entire content of which is hereby incorporated by reference.

Detection methods in general, and detection of analyst, surfactants, bacteria and diseases still present a significant challenge for a variety of industrial and medical applications.

One important field of application is the medical field, where the detection of bacteria and the detection of disease are important aspects thereof.

For example, somatic cells constitute of white blood cells—Macrophages and Leukocytes and Somatic Cell Counts (SCC) indicate the status of mammary gland as SCC increases during bacterial infection, and signifies an inflammation response. Mastitis is characterized by an increased number of inflammatory cells and SCC in milk. Accepted levels of SCC in milk globally range from 150,000 cells/mL (in Israel) to 400,000 cells/mL (in Europe) and 750,000 cells/mL (in the US).

While there are various techniques to measure SCC levels, most techniques cannot be easily implemented to provide accurate counting in "field" [i.e. farm] settings. One "on site" SCC measurement technique relies on measuring milk conductivity, which is related to SCC count. However, this technique usually cannot detect subclinical mastitis levels, and thus cannot tell if a cow is sick before it is taken out of milk production. Other techniques for detection of mastitis are based upon evaluating turbidity in milk samples—a relatively low sensitivity technique. Other approaches rely on indirect detection schemes—for example measuring concentrations of enzymes associated with occurrence of infections (such as lactate dehydrogenase). These techniques are generally expensive, labor intensive (milk samples are extracted from individual cows and tested), and rely on expensive laboratory instrumentation.

Other important analytical needs are the detection of various compounds and pollutants in water, such as surfactants, metals and heavy metals, oils, pesticides etc. Such target analytes are usually detected via dedicated instrumentation using often complex techniques that require technically-skilled operating personnel. Furthermore, varied analytes cannot be detected using field-operated instrumentation.

Thus, there is a continuing need to develop novel detection systems for disease, bacteria, and the presence of analytes.

In some applications, it is necessary to detect specific substrates, rather than the general detection of a family of compounds. For example, to detect a specific family of bacteria rather than to tell whether any bacteria is present.

Thus, there is another continuing need to develop novel specific detection systems for disease, bacteria, and the presence of analytes.

Polydiacetylenes (PDAs) are conjugated polymers displaying unique structural and chromatic properties which have attracted considerable interest as promising sensing platforms, primarily due to their visible and fluorescent color transformations (generally from blue to red), induced by varied external stimuli, such as heat, ionic strength, mechanical pressures and interactions with biological and chemical molecules. Modulation of the fluorescence emission of PDA systems which usually accompany the color changes has also contributed to progress in this field as the fluorescence phenomena opened routes for high sensitivity sensing and microscopic imaging.

Supported PDA films, in particular, exhibit distinct practical advantages, generally being robust and stable, and their molecular and macroscopic properties can be better controlled than vesicular systems. Solid-supported PDA films have been constructed via diverse techniques, including Langmuir monolayers, dip-coating, and spin-coating. For example, some of the present inventors have taught a colorimetric and/or fluorescent detector, which comprises a film of polydiacetylenes and lipids deposited on a glass substrate, and uses thereof as a colorimetric and/or fluorescent detector of bacteria (U.S. Pat. No. 8,008,039).

Poly(methyl methacrylate) (PMMA) is a generally transparent thermoplastic polymer and is the synthetic polymer of methyl methacrylate. It is sold under many different names, including, but not limited to, Acrylite™, Lucite™, and Perspex™.

Now, the present inventor presents a new chromatic PDA film system comprising of PDA/PMMA matrix, and shows that distinct color and fluorescence transitions were induced in this system by amphiphilic substances—surfactants and ionic liquids and that the chromatic transformations were correlated to the analyte structures and properties (this work has been published by the inventor in ACS Appl. Mater. Interfaces, 2014, 6 (11), pp 8613-8620).

BRIEF DESCRIPTION OF DRAWINGS

FIGS. 1A-1C depict an experimental scheme for spin coating two different PDA derivatives on PMMA, and the resultant film morphology.

FIG. 9A: unmodified PDA (TRCDA).

FIGS. 10A and 10E: PDA and FIG. 10F: PDA/PDA-PhB).

FIGS. 1A-1C depict an experimental scheme for spin coating two different PDA derivatives on PMMA, and the resultant film morphology. Two diacetylene monomers were employed: 10,12-tricosadiynoic acid displaying a carboxylic moiety, and 10,12-tricosadiyn amine in which the carboxylic residue was substituted with an amine. The monomers, dissolved in a THF/DCM mixture (1:1), were deposited through spin-coating upon circular-shaped PMMA substrates. Following drying and ultraviolet irradiation (254 nm), the PDA/PMMA films (produced by using only 10,12-tricosadiynoic acid), as well as PDA-NH2/PDA/PMMA (produced by using 1:9 mole molar ratio mixture of 10,12-tricosadiyn amine and 10,12-tricosadiynoic acid) turned intense blue due to the conjugated-system of the planar polydiacetylene network.

As outlined in FIG. 1A, the blue PDA/PMMA films underwent further colorimetric transformations into purple, red, or yellow, induced by external stimuli, as discussed in detail below. FIG. 1B-C present SEM images of the PMMA surface before and after spin coating, respectively. The initial PMMA surface was flat and uniform (FIG. 1B). Spin coating of PMMA with diacetylene and subsequent polymerization resulted in appearance of irregularly-shaped rectangular PDA domains previously detected in varied film and vesicle configurations (FIG. 1C).

FIGS. 2A-2D exemplify the new PDA/PMMA assembly developed in the present invention. In particular, they highlight the colorimetric transformations of PMMA-supported PDA films induced by heating and subsequent UV irradiation (similar results were recorded in case of spin coating of the PDA-NH$_2$/PDA mixture, data not shown). Following heating (5 minutes at 80° C.), the PDA/PMMA films underwent the well-known blue-red transformation[9] (FIG. 2A). Intriguingly, however, the red film became gradually purple upon subsequent irradiation with UV light (254 nm for 30 sec, FIG. 2A). It should be noted that longer irradiation times of the red PDA/PMMA films did not produce a complete back-transformation to blue color. Furthermore, the red-purple transformation was not affected by the extent of initial irradiation time—similar colorimetric results were recorded even when significantly longer initial irradiation was carried out (up to 10 minutes), making sure that complete PDA polymerization was achieved.

FIG. 2A discloses scanned images of PMMA-supported PDA films undergoing heat-induced blue-red transition and subsequent red-purple transformation induced by UV irradiation; FIG. 2B discloses UV-vis absorption spectra of the PMMA-supported PDA films shown in FIG. 2A; FIG. 2C discloses Fluorescence emission spectra of the PMMA-supported PDA films shown in FIG. 2A; FIG. 2D discloses Raman spectra of the PMMA-supported PDA films shown in FIG. 2A. The spectroscopic analyses in FIGS. 2B-2D indicate that the purple appearance corresponds to a back-transformation of the PDA film into a blue polymer phase. The UV-vis spectra in FIG. 2B confirm that UV irradiation resulted in re-emergence of the peak at around 650 nm corresponding to the blue PDA phase. Similarly, the fluorescence emission data in FIG. 2C reveal a dramatic attenuation of the PDA fluorescence of the red sample following UV irradiation, corroborating the hypothesis that the UV-induced purple phase of the PDA/PMMA film corresponds to a unique red-blue transformation of PDA. The Raman scattering data in FIG. 2D lend support to this interpretation, clearly showing that UV irradiation of the red PDA/PMMA films resulted in re-emergence of the prominent peaks at 1450 $cm^{-1}$ and 2090 $cm^{-1}$ associated with the blue PDA phase. Importantly, the red-purple transition was reversible, and the red phase of the film re-appeared after heating. It should be noted that the UV-induced reversible red-blue transition highlighted in FIGS. 2A-2D have not been previously reported in the literature for PDA films. This phenomenon is even more remarkable in light of the well-known effect of UV irradiation as an accelerant of blue-red transitions in PDA vesicles and films.

Figure 2A:
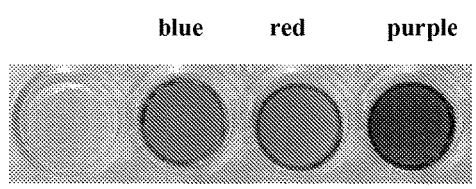
FIGS. 2A-2D exemplify a PDA/PMMA assembly.
Figure 2B:
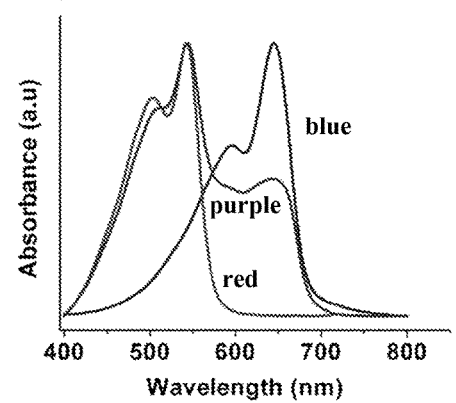
Figure 2C:
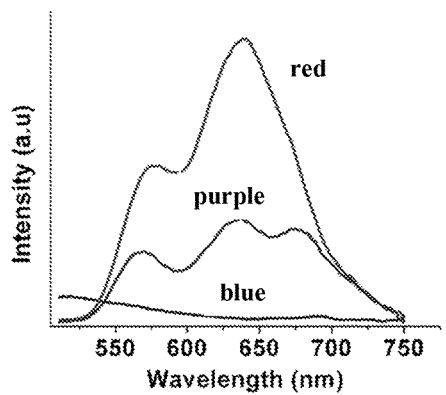
Figure 2D:
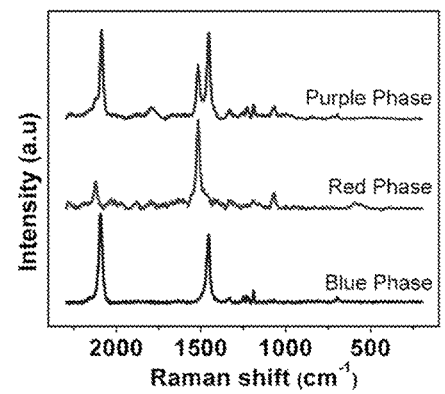

As can be seen in Examples 3-9 these detectors were successfully employed for detecting the presence of oils, surfactants, ion-pairs, heavy metals, bacteria, organophosphates etc.

Thus, according to one main aspect of the invention, there is now provided a colorimetric and/or fluorescent detector, which comprises a polydiacetylene (PDA) film deposited on a transparent polymethylmetacrylate (PMMA) substrate.

According to one preferred embodiment of the invention, this colorimetric and/or fluorescent detector is a solid organic matrix comprising one or more polydiacetylenes (PDA) deposited on a polymethylmetacrylate (PMMA) surface, wherein the PDA comprises polymerized units of one or more diacetylene monomers.

By the term "colorimetric and/or fluorescent detector" is meant that the aforementioned system comprising polydiacetylene(s) on a PMMA substrate is capable of responding to the presence of various analytes by exhibiting a chromatic transition (e.g. a change in visible color of the matrix or a portion thereof) and/or a characteristic fluorescent emission associated therewith.

As used herein, the term "direct colorimetric detection" refers to the detection of color changes without the aid of an intervening processing step (e.g. conversion of a color change into an electronic signal that is processed by an interpreting device). It is intended that the term encompass visual observing (e.g., observing with the human eye) as well as detection by simple spectrometry.

The term "solid organic matrix", as used herein, indicates a solid framework made of organic compounds and, more specifically, organic polymers, wherein these polymers are polydiacetylene polymers deposited on a polymethylmethacrylate surface, whereas these polymers interchelate and/or interact with the PMMA surface and together form the solid framework of the detector. The term "polymers", as used herein, encompasses both homopolymers and copolymers.

The polydiacetylenes which form part of the present invention are polymers of one or more diacetylene monomers.

In particular, the organic matrix of the present invention comprises a plurality of polymerized self-assembling diacetylene monomers.

Preferably, the diacetylene monomers are deposited as a film on the PMMA substrate, to form the PDA/PMMA matrix of the present invention.

It should be noted that the term "polydiacetylene film" is used herein in a non-limiting way and means one or more thin polydiacetylene layers of uniform thickness.

While in most cases the PDA was deposited on a pre-polymerized PMMA surface, it may also be possible to co-polymerize the diacetylene monomers along with self-assembling methacrylate monomers, to form the PDA/PMMA matrix of the present invention.

The term "diacetylene monomer" as used herein embraces all the compounds having a conjugated diacetylene linkage inclusive of various derivatives thereof.

Diacetylene monomers are characterized by the length of the carbon chains on each side of the two aceytylene groups, the head groups at each end of those chains, and by the distance of the two aceytylene groups from each head group.

Their general structure can be described as shown in Formula I below:

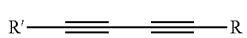

Formula I

Whereas upon polymerization, a conjugated polydiacetylene polymer is obtained, as shown in Scheme 1 below:

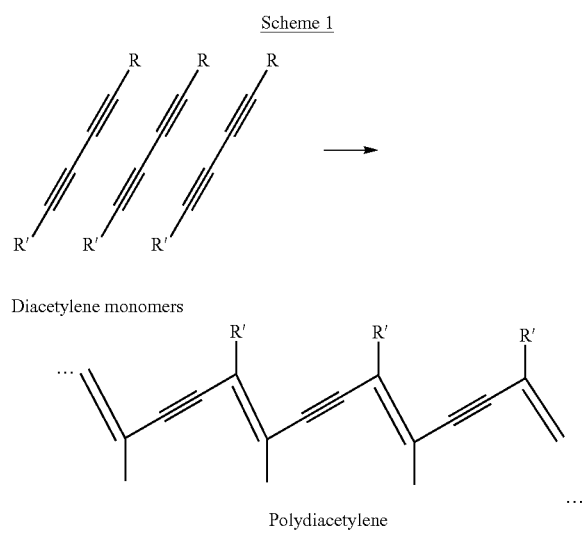

The type of the R and R' carbon chains vary, such that one of them may end with a head group, such as a carboxylic head group, while the other chain ends with a hydrophobic terminus.

The general know-how in the field of diacetylene polymerization recommends that the size of the head group at the end of the R and R' carbon chains will not be too bulky for an effective polymerization to take place. Similarly, it is believed that a head group cannot be too close to the acetylene bonds, namely it is preferably not closer than 4 carbon-carbon bonds from the head group.

The term "head group" as used herein refers to the molecular group present at one or both ends of the diacetylene monomer, namely the group that is attached to the last carbon on one side of the carbon chains, while the 2$^{nd}$ chain ends with a hydrophobic terminus group.

Some diacetylene monomers that may be used according to the present invention for preparing the chromatic polydiacetylenes of the present invention are well known in the art and are described, inter alia, in WO 99/10743, and US 2002/0034475, to name a few, which are incorporated herein by reference. However other diacetylene monomers may be used and chosen by any person skilled in the art.

In many of these monomers, at least one of R or R' ends with a carboxylic head group.

Some preferred examples of diacetylene monomers ending with carboxylic head groups and suitable for the present invention are selected from the group comprising of, but not limited to, 10,12-tricosadiynoic acid, 10,12-pentacosadiynoic acid, 10,12-octadecadiynoic acid, 5,7-docosadiynoic acid, 5,7-pentacosadiynoic acid and 5,7-tetracosadiynoic acid. These monomers are all commercially available. As known to a person skilled in the art, other diacetylene monomers can be synthesized and used.

In one convenient, yet non-limiting example, the diacetylene monomer is 10,12-tricosadiynoic acid (TRCDA) which is the "basic" diacetylene monomer, and is also used for further derivatization.

Diacetylene monomers comprising other head groups may also be suitable for the present invention.

In particular, the inventors have shown that in some cases, especially for the detection of amphiphilic compounds, the addition of a diacetylene monomer having a hydrophilic head group enhanced the sensitivity of the detector.

For example, it has been found that incorporation of an amine-head group polydiacetylene denoted PDA-TEA, in addition to the unmodified diacetylene, increased the sensitivity of the detector to the presence of lanthanides.

In another example (Example 3), it was shown that pure PDA coatings (namely, with no amine-diacetylene monomers being polymerized) appeared to be not sufficiently sensitive to the infected milk under the experimental conditions. It was further found that based on recorded color changes, the 20% amine-PDA containing circles (Formulation 1) were more sensitive to the examined milk samples than the 10% amine-PDA coatings (Formulation 2): Basically the blue-red transitions in formulation 1 are more significant. This can also be deducted from the percentage values shown in FIGS. 3A and 3B. In both cases the color was redder as the SCC concentration was higher.

It can generally be noted that diacetylene monomers having small and hydrophilic head groups are easily polymerizable and can potentially have strong colors, which increases their detection sensitivity and effectiveness as colorimetric detectors.

The term "hydrophilic head-group" refers to head groups that are substantially attracted to water by chemical interactions. Examples of suitable hydrophilic head groups according to the present invention include, but are not limited to, a carboxylic acid group, a carboxy group, an amino group, a polyethylene oxide group, a polypropylene oxide group, a hydroxy group, a sulfonic acid group, an amide group, a sulfate group, a substituted amide group, a phosphate group and an ammonium salt group.

The term "small hydrophilic head group", as used herein, refers to a head group which contains up to 5 atoms.

As can be seen in Examples 3-9 which follow, the polydiacetylene can be composed by polymerized diacetylene monomers having only a small hydrophilic head group, or may also contain diacetylene monomers having other head groups, which are not necessarily hydrophilic or are not necessarily small, and may even contain other molecules within the matrix, which act as recognition elements and are also not necessarily hydrophilic or are not necessarily small.

While the addition of a sterically hindered monomer or another polymer or a large organic molecule during the polymerization stage, has a high potential to adversely affect the rate and level of polymerization, and hence the colorimetric properties of the matrix, the inventors have found a balanced ratio between the amount of diacetylene monomers having small hydrophilic head groups and the amount of diacetylene monomer having head groups that are either large or non-hydrophilic, and/or recognition element, this matrix having an enhanced selectivity and sensitivity, yet maintains a high polymerization level and hence good chromatic properties.

A variety of head groups and recognition elements have been tested, in a range of concentrations concluding that in these cases, since the polymerization may be adversely affected by hydrophobic interactions and/or by steric hindrance, preferably the PDA matrix comprises at least 40 mole percent of polymerized diacetylene monomers having small (namely having up to about 5 atoms) and hydrophilic head groups. This includes matrices having 100% polymerized diacetylene monomers having small hydrophilic head groups, but also includes any combination of head groups and/or recognition elements, as long as about 40 mole percent of the PDA matrix comprises PDA composed of monomers having small hydrophilic head groups.

Thus, according to one preferred embodiment of the present invention, the PDA comprises at least 40 molar percent of polymerized units of a diacetylene monomer having a hydrophilic head group, further wherein this head group comprises up to 5 atoms.

Preferably, the percent of polymerized units of a diacetylene monomer having a hydrophilic head group ranges from about 40 molar percent up to 100 molar percent.

In some preferred embodiments of the invention, it ranges from about 40 molar percent up to 90 molar percent.

In some more preferred embodiments of the invention, it ranges from about 50 molar percent up to 70 molar percent.

In many of the examples a mole ratio of 50%-50% of diacetylene monomers having a hydrophilic head group and diacetylene monomers having other head groups has been used.

As can be seen in the Examples section which follows, a large number of diacetylene derivatives have been prepared, as detailed in Table 1 below. These derivatives have different head groups, such as aliphatic, aromatic, amine, alcohol and fluorine-containing

TABLE 1

| Short Name | Head Group class | Structure | Chem. Name |
|---|---|---|---|
| TR—CDA | Carboxylic acid | 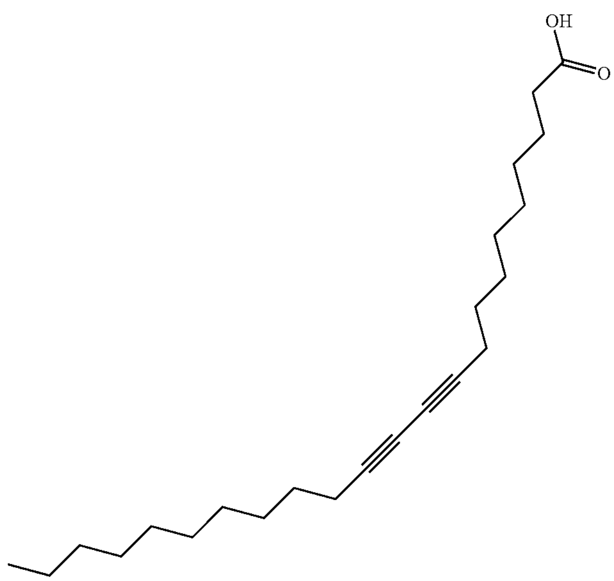 [SMILES: CCCCCCCCCCC#CC#CCCCCCCCCC(=O)O] | 10,12-tricosadiynoic acid (TRCDA) |
| TR—OH | Alcohol | 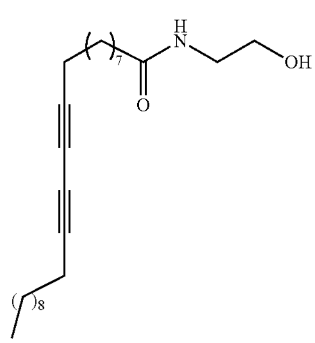 | N-(2-ethanol)docosa-10,12-diynamide |

TABLE 1-continued

| Short Name | Head Group class | Structure | Chem. Name |
| --- | --- | --- | --- |
| TR-Leu | Aliphatic | 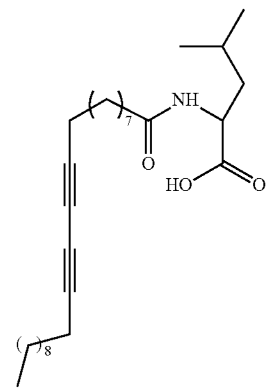 | 2-(docosa-10,12-diynamido)-4-methylpentanoic acid |
| TR-MLeu | Aliphatic | 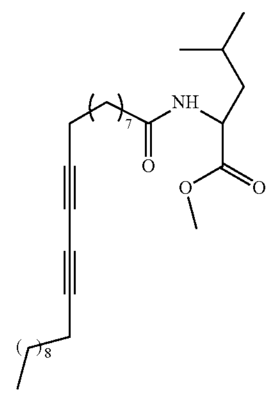 | methyl-2-(docosa-10,12-diynamide)-4-methylpentanoate |
| TR-amine | Amine | 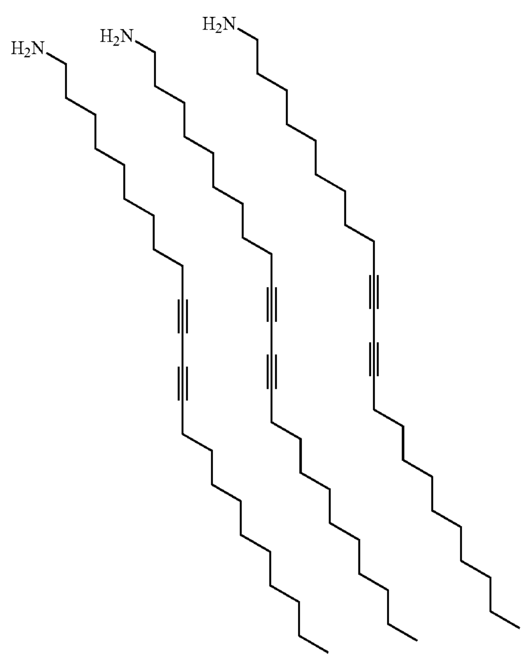 [SMILES: CCCCCCCCCCC#CC#CCCCCCCCCCN ; CCCCCCCCCCC#CC#CCCCCCCCCCN ; CCCCCCCCCCC#CC#CCCCCCCCCCN] | 10,12-tricosadiyn amine |

TABLE 1-continued

| Short Name | Head Group class | Structure | Chem. Name |
|---|---|---|---|
| TR—EDA TR—TEA | Amine | 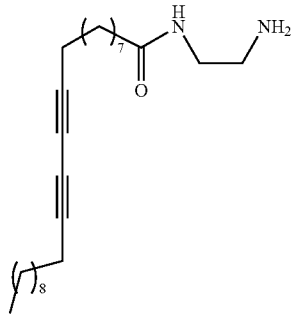 | N-(2-aminoethyl)docosa-10,12-diynamide |
| TR—N3 TR—TDEA | Amine | 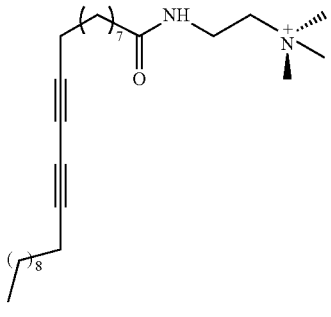 | 2-(docosa-10,12-diynamido)-N,N,N-trimethylethanaminium |
| TR-MLys | amine | 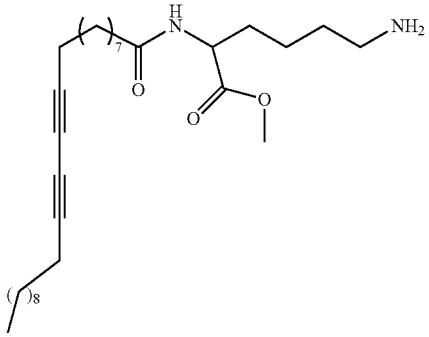 | methyl 6-amino-2-(docosa-10,12-diynamido)hexanoate |
| TR-Phe TR—phA | aroatic | 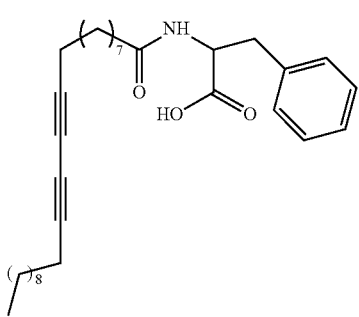 | 2-(docosa-10,12-diynamido)-3-phenylpropanoic acid |
| TR-Mphe TR—MPhA | aroatic | 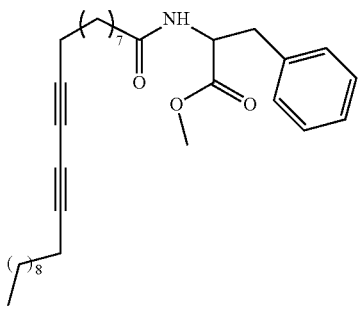 | methyl 2-(docosa-10,12-diynamido)-3-phenylpropanoate |

TABLE 1-continued

| Short Name | Head Group class | Structure | Chem. Name |
|---|---|---|---|
| TR—PhB | Aromatic Boronic acid | 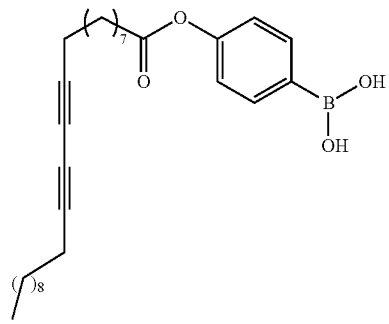 | (4-(docosa-10,12-diynoloxy)phenyl)boronic acid |
| TR—NaPh | Aromatic | 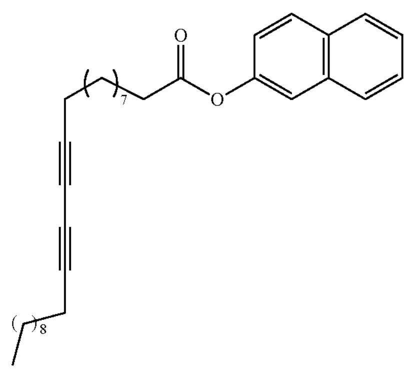 | naphthalen-2-yl tricosa-10,12-diynoate |
| TR—F3 TR—Flu | Fluoro (polaric) | 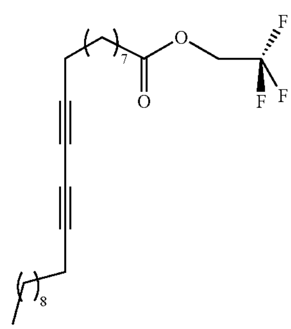 | 2,2,2-trifluoroethyl docosa-10,12-diynoate |
| TR—F10 | Fluoro (polaric) | 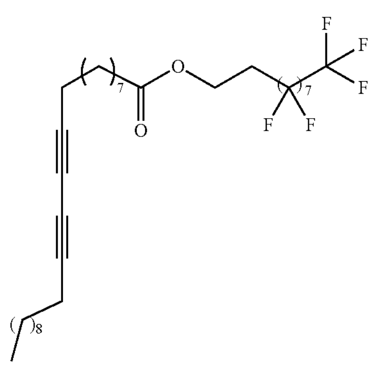 | 3,3,4,4,5,5,6,6,7,7,8,8,9,9,10,10-heptadecafluorodecyl docosa-10,12-diynoate |

TABLE 1-continued

| Short Name | Head Group class | Structure | Chem. Name |
|---|---|---|---|
| TR-iF6 | Fluoro (polaric) | 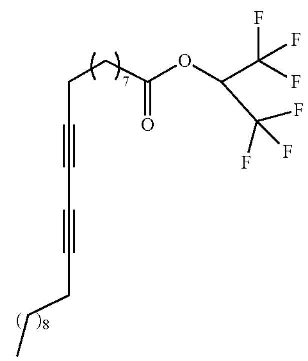 | 1,1,1,3,3,3-hexafluoropropan-2-yl docosa-10,12-diynoate |

As noted hereinabove, in one preferred embodiment of the present invention, the hydrophilic head group is a carboxylic acid group.

One example of this type of diacetylene monomer is 10,12-tricosadiynoic acid (TRCDA).

Therefore, according to one preferred embodiment, there is provided the colorimetric and/or fluorescent detector described herein, wherein the PDA comprises polymerized units of an 10,12-tricosadiynoic acid (TRCDA) monomer.

In another preferred embodiment of the present invention the hydrophilic head group is an amine group.

Some examples of this type of diacetylene monomer are selected from: 10,12-tricosadiynamine (PDA-amine), N-(2-aminoethyl)docosa-10,12-diynamide, 2-(docosa-10,12-diynamido)-N,N,N-trimethylethanaminium, and methyl 6-amino-2-(docosa-10,12-diynamido)hexanoate.

In yet another preferred embodiment of the present invention the hydrophilic head group is a hydroxy group.

One example of this type of diacetylene monomer is N-(2-ethanol)docosa-10,12-diynamide.

Examples 3-9 present successful detectors that were prepared by using a matrix comprising PDA/PMMA, whereas the PDA was composed of either one or more polymerized diacetylene monomers, some of which containing these hydrophilic groups.

It should be noted that the detector can be either in a form of a planar structure or of a non-planar structure, such as beads.

In most applications as a colorimetric detector, the PMMA surface on which said PMA is deposited and which forms part of the solid matrix of the invention is preferably a transparent surface.

As used in this specification, the term "transparent" with regard to the PMMA transparent surface, means substantially transparent or translucent.

However, depending on the preparation method and its required form, the PMMA may also be used as a non-transparent substrate, for example as beads.

As also noted hereinabove, in some cases the diacetylene monomers were combined with one or more molecular recognition elements.

The term "recognition element" as used herein refers to a molecular residue which has some structural or steric affinity to an analyte, and hence recognizes and selectively binds to this analyte.

In particular, the recognition element has one or more functionalities and/or ligands which are capable of binding to an analyte, such that binding of an analyte to the ligand causes a conformational change in the polymerized self-assembling PDA monomers, resulting in a color change and/or a fluorescent change of the film.

As used herein, the term "ligands" refers to any ion, molecule, molecular group, or other substance that binds to another entity to form a larger complex. Examples of ligands include, but are not limited to, peptides, carbohydrates, nucleic acids (e.g., DNA and RNA), antibodies, or any molecules that bind to receptors.

The recognition element can be selected from a wide variety of molecular residues.

For example, according to one preferred embodiment, the recognition element is selected from the group consisting of: an aromatic recognition element, an aliphatic recognition element, a halogen recognition element, an amino acid recognition element or combinations thereof.

The scope of these groups is well known to a person skilled in the art.

As used herein, the term "analyte" refers to any material that is to be analyzed. Such materials include, but are not limited to, ions, molecules, antigens, bacteria, compounds, viruses, cells, antibodies, and cell parts.

According to one preferred embodiment of the invention, the analyte is selected from the group consisting of surfactants, ions, oils, microorganisms and toxins produced thereby, metal cations, peptides, organophosphates, organic pollutants, chemical agents, others pharmaceutically active compounds, proteins and biological ligands.

In one example, this recognition element may be a head group of the diacetylene monomer, having some kind of Van-der-Waals or hydrophobic interactions with the target analyte.

Therefore, according to preferred embodiments of the present invention, the matrix comprises of polymerized diacetylene monomers having at least one recognition element as a head group of the diacetylene monomers.

Examples of suitable head groups which may serve as recognition elements according to the present invention include, but are not limited to hydrophobic groups, such as aliphatic, aromatic, and halogen groups, but may also be large yet not hydrophobic groups, such as polar residues, chelators, macromolecular binding pockets, or any combinations thereof.

In one preferred embodiment, the recognition element is an aromatic head group. Some exemplary diacetylene monomers having at least one aromatic head group and successfully used in the present invention include, but are not limited to, 2-(docosa-10,12-diynamido)-3-phenylpropanoic acid, methyl 2-(docosa-10,12-diynamido)-3-phenylpropanoate, and (4-(docosa-10,12-diynoloxy)phenyl)boronic acid. These monomers formed part of a detector for the detection of organophosphates.

In one preferred embodiment, the hydrophobic head group is a halogen head group. More preferably, the halogen head group is a fluorine head group.

Some examples of diacetylene monomers having at least one fluorine recognition element as a head group that were successfully used in the present invention include, but are not limited to: 2,2,2-trifluoroethyl docosa-10,12-diynoate, 3,3,4,4,5,5,6,6,7,7,8,8,9,9,10,10-heptadecafluorodecyl docosa-10,12-diynoate, and 1,1,1,3,3,3-hexafluoropropan-2-yl docosa-10,12-diynoate. These monomers formed part of a detector for Fluorogenic substates.

In another preferred embodiment, the recognition element is an aliphatic head group. Some examples of diacetylene monomers having at least one aliphatic head group as a recognition element and successfully used in the present invention include, but are not limited to 2-(docosa-10,12-diynamido)-4-methylpentanoic acid, and methyl-2-(docosa-10,12-diynamide)-4-methylpentanoate. These monomers formed part of a detector for aliphatic organophosphates.

In one preferred embodiment of the present invention, the diacetylene monomers containing recognition elements as head groups are selected from, yet not limited to, 2-(docosa-10,12-diynamido)-3-phenylpropanoic acid, methyl 2-(docosa-10,12-diynamido)-3-phenylpropanoate, (4-(docosa-10,12-diynoloxy)phenyl)boronic acid, 2,2,2-trifluoroethyl docosa-10,12-diynoate, 3,3,4,4,5,5,6,6,7,7,8,8,9,9,10,10-heptadecafluorodecyl docosa-10,12-diynoate, 1,1,1,3,3,3-hexafluoropropan-2-yl docosa-10,12-diynoate, 2-(docosa-10,12-diynamido)-4-methylpentanoic acid, and methyl-2-(docosa-10,12-diynamide)-4-methylpentanoate.

Clearly, an endless number of suitable recognition element head groups can be devised and synthesized, according to the specific need or application, and the examples provided below should not be limiting in any way.

In another preferred embodiment of the invention, the recognition element forms part of the matrix, without actually being covalently attached to the PMA or to the PMMA.

Examples of this type of recognition elements include, but are not limited to, membrane-associated receptors, synthetic receptors, antibodies and the antigen-binding sites derived therefrom. Recognition elements also include receptors and the receptor binding sites derived therefrom. Other recognition elements include ionophores and chelators.

Some examples of recognition elements that were successfully used in the present invention include, but are not limited to, Monensin, thenoyltrifluoroacetone (TTA) and 1,10-bis(thiophene-2'-yl)-4,4,5,5,6,6,7,7-octafluorodecane-1,3,8,10-tetraone (BTOT).

Inclusion of these recognition elements resulted in a system having chromatic reversibility induced by ultraviolet (UV) irradiation, and purple/red/orange/yellow color transformations and fluorescence transformations affected by interactions with a large variety of analytes.

Monensin is an ionophore related to crown ethers with a preference to form complexes with monovalent cations such as: $Li^+$, $Na^+$, $K^+$, $Rb^+$, $Ag^+$, and $Ti^+$. The antibacterial properties of monensin and its derivatives are a result of their ability to transport metal cations through cellular and subcellular membranes.

Figure 5:
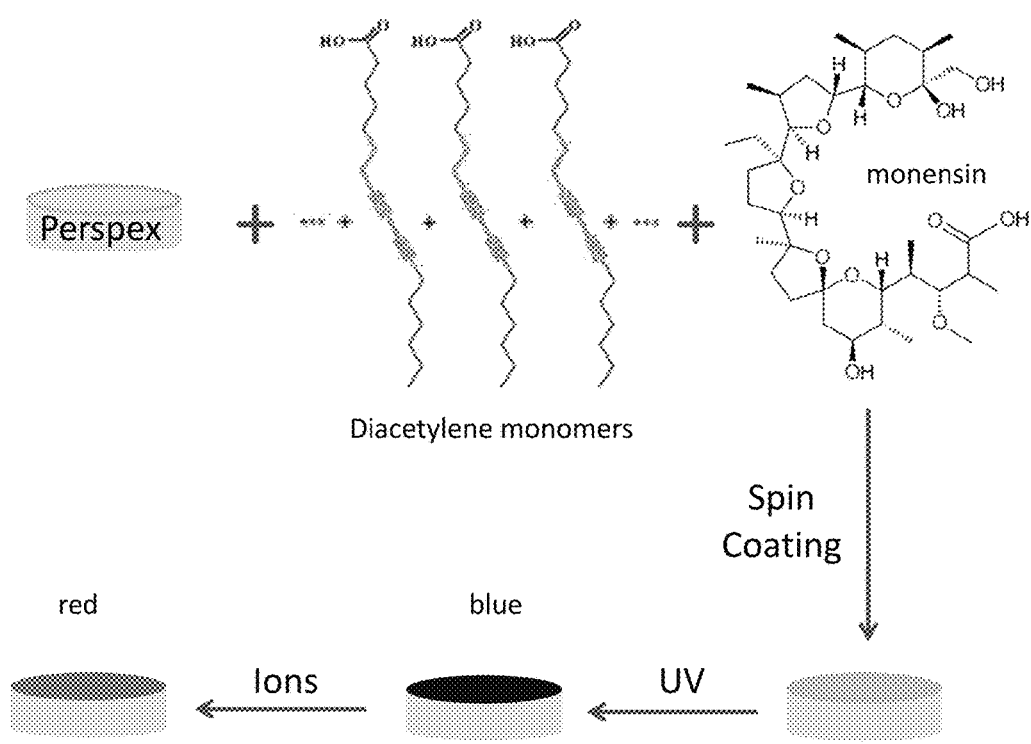
FIG. 5 depicts an experimental scheme for spin coating different PDA derivatives along with an ionophore (monensin molecule), on PMMA, and the use thereof in detecting the presence of ions.

FIG. 5 depicts an experimental scheme for spin coating different PDA derivatives along with an ionophore (monensin molecule), on PMMA, and the use thereof in detecting the presence of ions. It was now shown (Example 6) that the addition of Monensin either alone or in combination with PE during the polymerization of the diacetylene monomer was successfully used for the detection of ions in water.

Figure 6:
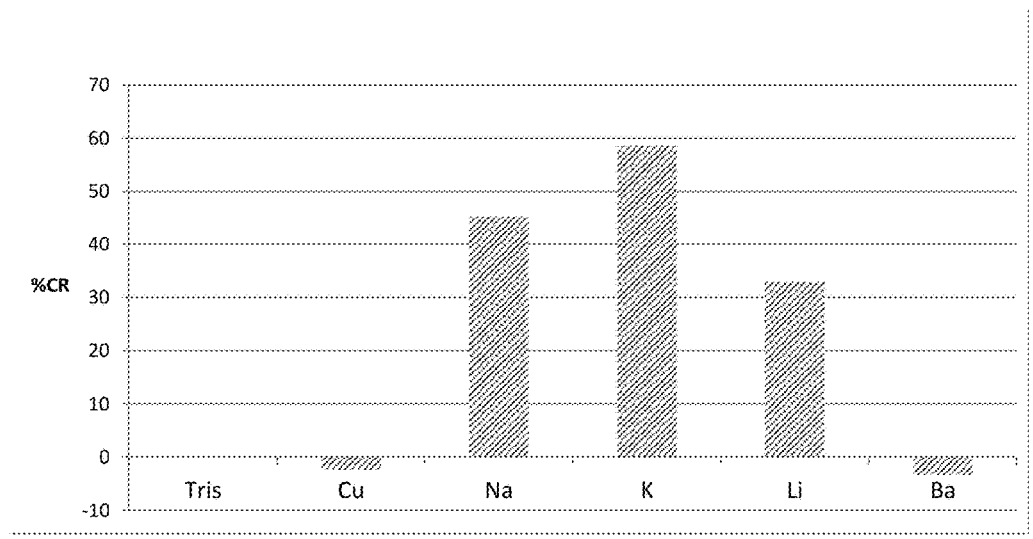
FIG. 6 discloses the % CR of PDA/Monensin (at 27/18 mg/ml) on a PMMA substrate, after 2 hours.

FIG. 6 discloses the % CR of PDA/Monensin (at 27/18 mg/ml) on a PMMA substrate, after 2 hours. In particular, as can be seen in FIG. 6 chromatic transformations were directly related to the presence of the ionophore (monensin) associated with PDA in the films. Specifically, more pronounced red absorbance and fluorescence emission (at 560 nm and 640 nm) were recorded in case of PDA/monensin films as compared to pure PDA films. Moreover, more pronounced chromatic transformations were induced upon addition of $K^+$ and $Na^+$ ions to PDA/monensin—which are the alkali metal ions specifically recognized by monensin.

Thus, according to one preferred embodiment of the invention, the recognition element is an ionophore.

The term "ionophore" refers to a compound that binds and carries metallic ions across cellular membranes. Ionophores can be used for the detection and selective binding process of an ion of interest.

Examples of ionophores for sulfate detection are zinc phthalocyanine and 1,3-[bis(3-phenylthioure-idomethyl)] benzene. Examples of ionophores for chloride detection include 4,5-bis-[N'-(butyl)thioureido]-2,7-di-tert-butyl-9,9-dimethylxanthene and meso-tetraphenylporphyrin manganese (III). Examples of ionophores for zinc detection include 3-[(2-furylmethylene)amino]-2-thioxo-1,3-thiazolidin-4-one and 1-(2-pyridylazo)-2-naphthol.

BTOT is a synthetic chelator composed of two units of TTA separated by a spacer, which does not contain additional donor groups. In this recognition system the two beta-diketones facilitate formation of binuclear complexes in which the two bound metal ions do not interact with each other, thereby increasing the chelating power of the ligand.

Preliminary colorimetric experiments (see Example 7) were conducted for the detection of lanthanide ions using PDA matrixes comprising different combinations of PDA, TTA, and BTOT. The color changes reflect interactions of the ions with the receptor units, thereby inducing the structural/chromatic transitions of PDA. Notably, the scanned films in FIG. 14 demonstrate that different color changes were induced by specific ions. This observation is likely related to the affinities of the ions to the embedded receptors and suggests that the PDA film platform is capable of distinguishing among different ions. The colorimetric data in FIG. 14 indicate that the PDA platform indeed responds to lanthanide ions, and that selectivity of the PDA system can be accomplished through incorporation of derivatized diacetylene receptors and tuning of the PDA matrix composition.

Thus, according to one preferred embodiment of the invention, the recognition element is a chelator.

As used herein, the term "chelator" refers to any molecule which possesses at least one functional group which can coordinate to a metal, either covalently or non-covalently. The chelator may be multidentate or coordinate in a unidentate manner.

The chelator may be a macrocycle such as a porphyrin. The chelator may chelate a metal by donating or sharing pi electrons. Chelators further derivatized to increase spectroscopic detection are also included. The functional group of the chelator may be negatively or positively charged, or neutral. Examples of suitable functional groups include carboxylato, thiolato, hydrido, cyano, carbonato, thiocarcamato, thiocarboxylato, thiophosphinato amino, phophoro, hydrazino, nitrilo, hydrazido, oxime, and thioether.

Other examples of chelators include ethylenediaminetetraacetic acid (EDTA), diethylenetriaminepentaacetic acid (DTPA), ethylene, and ethylene glycol-bis(2-aminoethylether)-N,N,N',N'-tetraacetic acid (EGTA).

While certain modified PMAs and recognition elements have been exemplified hereinbelow, it is clear to a person skilled in the art that a number of recognition elements of this type can be used, depending on the exact needs of the detection, and therefore one of ordinary skill in the art would understand that such examples are not meant to be limited to specific recognition elements.

According to some preferred embodiments, the detector further comprises one or more non-polymeric additives.

As used herein, the term "additives" refers to molecules that are added to the diacetylene monomers during polymerization to change the properties of the PDA/PMMA system. Such properties include, but are not limited to, fluidity, calorimetric response, color, sensitivity, durability, robustness, amenability to immobilization, temperature sensitivity, and pH sensitivity.

In particular, it is often desired to increase the fluidity of the aforementioned detector systems, since higher mobility of the polymeric chains will result in more pronounced color and therefore higher sensitivity of the system to target analytes.

The term "fluidity" is intended to refer to the ability of the polymer components to undergo molecular motion with respect to one another. The ability will depend upon the polymer's particular configuration, i.e. linear or branched, crystalline or amorphous, degree of crosslink, temperature of the composition and the like. The fluidity can be measured by conventional techniques such as using Standard Load Melt Index of High Load Melt Index tests (ASTM D-1238-57T) modified to be measured at varying temperatures.

Some Additives that can increase the fluidity of the PDA include, but are not limited to, surfactants, lipids, fatty acids, and peptides.

As exemplified hereinbelow, the inventors have now shown that the afore-mentioned detectors can be successfully employed for the detection of a large number of analytes in a variety of samples, both in non-specific and specific manners.

First, it was shown that using a PDA/PMMA detector wherein at least some of the diacetylene monomers had hydrophilic head groups, (such as carboxylic acid or amine head groups), can be used for the general detection of the presence of an analyte or family of analytes in a tested sample.

The detector comprising solely of polymerized diacetylene monomers having small hydrophilic head groups on a PMMA surface has been successfully used for the non-specific detection of analytes, such as the detection of SCC in milk, for the detection of bacteria in water and for the detection of surfactants in water (see Examples 3, 4 and 5).

In all of these cases, the hydrophilic head groups resulted in non-specific interaction of the detector and the analyte, such as electrostatic attraction or hydrophobic interactions. These interactions are arbitrary and are not based on structural compatibilities of the molecules.

In other cases, for example when a recognition element was added to the matrix, either as a head group of the diacetylene monomer, or on its own, a more specific detection can occur.

Figure 14:
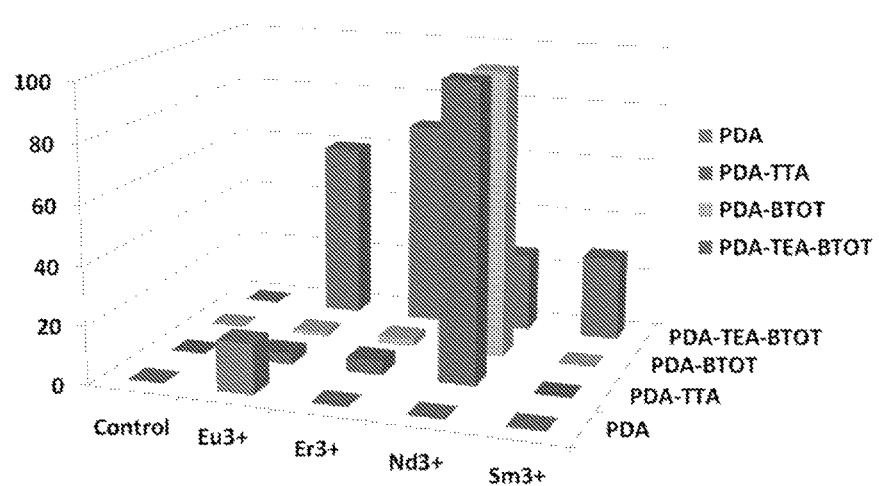
FIG. 14 shows that different color changes are induced by specific ions.

For example, as taught in the experimental section hereinbelow, specific interactions were used to detect the presence of oils and/or pesticides in water, as well as to enhance the detection of ions in water through the addition of ionophores. In another example, it was shown that lanthanide ions interacted with BTOT receptor units, thereby inducing the structural/chromatic transitions of PDA (FIG. 14).

In both specific and non-specific detection, the method of detection is based on the addition of an analyte sample to the detector, an incubation period and observance or measurement of the color change.

As used herein, the term "selective detection" or "selective binding" refers to the binding of one material to another in a manner dependent upon the presence of a particular molecular structure (i.e., specific binding). For example, a receptor will selectively bind ligands that contain the chemical structures complementary to the ligand binding site(s). As noted above, this is in contrast to "non-selective binding," whereby interactions are arbitrary and are not based on structural compatibilities of the molecules. Selective detection is based upon molecular interactions between distinct molecular units. For example, when the molecular units are aromatic residues, the detector is expected to specifically detect aromatic analytes.

Therefore, according to one aspect of the invention, there is now provided a method for detecting the presence of an analyte in a sample, this method comprising contacting the sample with any of the detectors described herein, and following an incubation time, either observing or measuring the color of the matrix or detecting a fluorescent emission thereof, wherein a change in the color or a characteristic fluorescence emission indicate the presence of the analyte in the sample The term "presence of an analyte" should be construed as referring to the qualitative presence or absence of an analyte in a sample, but can be quantified if needed.

As used herein, the term "sample" is used in its broadest sense and includes any liquid sample, in particular aqueous samples. The term sample includes, but is not limited to, biological samples and environmental samples.

Biological samples include any number of biological fluids. Non-limiting examples of biological fluids include serum, plasma, whole blood, urine, saliva, milk, tears, sweat, joint fluid, cerebrospinal fluid, semen, vaginal fluid, ascetic fluid and amniotic fluid.

Environmental samples include environmental material such as surface matter, soil, water, crystals and industrial samples. These examples are not to be construed as limiting the sample types applicable to the present invention.

According to preferred embodiments of the present invention, analytes suitable for detection according to the methods of the present invention are selected from the group consisting of surfactants, ions, oils, microorganisms and toxins produced thereby, metal cations, peptides, organophosphates, organic pollutants, chemical agents, others pharmaceutically active compounds, proteins and biological ligands. However, as known to a person skilled in the art, additional analytes may be suitable for detection according to the present invention, and therefore these examples are not to be construed as limiting the analyte types applicable to the present invention.

As used herein, the term "incubation time" refers to the time it takes the analyte to be tested to sufficiently interact with the PDA/PMMA matrix, to confirm a negative colorimetric response of the analyte with the matrix. Namely, measuring the color change after the incubation time is expected to provide a reliable detection result regarding the presence or absence of the analyte in the tested sample.

As seen for example in the surfactant experiment, some color change may also evolve for the control (in this happened after 150 minutes), due to temperature, salts and the cells present in the control. Therefore, the shorter the detection time the lesser color transition of the control.

According to one preferred embodiment of the invention, the incubation time ranges from 10 seconds to 3 hours.

In one preferred embodiment, an incubation time of about 60 minutes is used.

In most cases an incubation time of about 20 minutes was sufficient, and therefore in another preferred embodiment the incubation time is less than 30 minutes.

As shown in the experimental section which follows, the detection methods described hereinabove were able to detect analytes at concentrations as low as 20 ppm (in the organophosphate detection experiment). The sensitivity of the detection can be enhanced by increasing the fluidity/elasticity of the detector system, for example by the addition of sterically hindered head groups.

For many applications, in particular for biological samples and environmental samples, it is necessary to obtain a detection limit no higher than 20 ppm, more preferably no higher than 10 ppm, and more preferably, no higher than 1 ppm.

Thus, according to one preferred embodiment of the invention, the method described herein has a detection limit of 10 ppm, more preferably a detection limit of 1 ppm.

The term "detection limit" is used to describe the lowest analyte level that can be confidently identified and/or detected but not necessarily quantified.

Some specific examples of detection methods according to the present invention, will now be disclosed in detail.

One application of the non-specific detection of the present invention is provided in Example 4 hereinbelow, when the detection of bacteria in water, since it has now been further found that the polymer system of the present invention changes color when in contact with bacteria and can therefore be useful for the detection of bacteria.

According to this method, bacterial cells in water can be detected, making the PDA/PMMA a useful visual and spectroscopic sensor for bacteria in various solutions.

Another application of the non-specific detection of the present invention is provided in Example 3 hereinbelow, for detecting subclinical-to-clinical levels of Somatic Cell Counts (SCC) in milk samples.

It has now been further found that the polymer system of the present invention changes color when in contact with SCC cells. The higher the concentration of cells the faster and more pronounced is the color change. Furthermore, it has been found that the red form of the polymer fluoresces strongly when exposed to short wavelength (e.g. blue) light, while the blue form of the polymer does not fluoresce. These properties enable to use the polymer system in the detection of mastitis in cows. The main advantage of the PDA-based sensor—extremely cheap and robust, on-site visual detection is available, possible to couple to milking apparatus.

According to this method, the non-specific detection of SCC in milk is conducted by first contacting a milk sample with the polydiacetylene film of the aforementioned non-specific detector, and letting this sample incubate for an incubation time of at least 20 minutes.

This is followed by inspecting the color of the film after the incubation time and comparing it to a detector contacted by a control sample containing up to 20,000 SCC cells/mL, whereby a visual red color indicates high levels of SCC and a visual blue or purple color indicates normal levels of SCC.

Alternatively, the color change and/or fluorescence can be measured by methods known in the art.

For example, the color change can be measured by UV-Vis spectroscopy, color scanning, etc, in which case one does not need direct comparison to control.

In one embodiment of the invention, the fluorescence of the film is measured after excitation at between 450 nm and 500 nm, whereby a fluorescence of more than 5 units indicates high levels of SCC and a fluorescence of less than 5 units indicates normal levels of SCC.

Detecting high levels of SCC in milk samples can signal that a certain milk sample belongs to a cow infected by mastitis, which should therefore not be used.

The presence of SCC can be detected either by colorimetry or through fluorescence (excitation 480 nm, emission, 560-640 nm, but other wavelengths are also possible). Fluorescence may be even more sensitive than colorimetry.

It should be noted that the method can be turned into a specific-detection by using a PDA comprising of suitable SCC recognition elements. It is expected that using this method will result in enhanced sensitivity, as compared to the non-specific method.

One other detection method based on the detectors of the present invention is for the detection of surfactants and/or ions and/or metals and/or pollutants in water.

For example, the inventors have now investigated the chromatic response of the new PMMA-supported PDA films upon addition of different analytes (FIGS. 3-4). The PDA/PMMA film assemblies are particularly attractive as a sensing platform since they are physically robust and stable, exhibit color durability for long time periods (months) and are amenable for mass production. Scheme 1 presents the structures of representative amphiphilic molecules tested in this study. Specifically, various amphiphilic compounds (compounds 1-10, scheme 2) were examined belonging to different classes, including cationic surfactants [1-hexadecyltrimethylammonium bromide (CTAB) 1, and cetylpyridinium chloride (CPC) 2], ionic liquids (ILs) [1-dodecyl-3-methylimidazolium chloride (C12mimCl) 3, and 1-hexadecyl-3-methylimidazolium chloride (C16mimCl) 4], weak acid/base surfactants [dodecylamine, 5, 1-lauryl-4-carboxy-2-pyrrolidone (ITAC12) 6], non-ionic surfactants [4-O-lauryl-1,6-anhydroglucopyranose (C12LG) 7, and Triton X-100 8] and anionic surfactants [sodium dodecylsulfate (SDS) 9 and sodium dodecylbenzenesulfonate (SDBS) 10].

Scheme 2

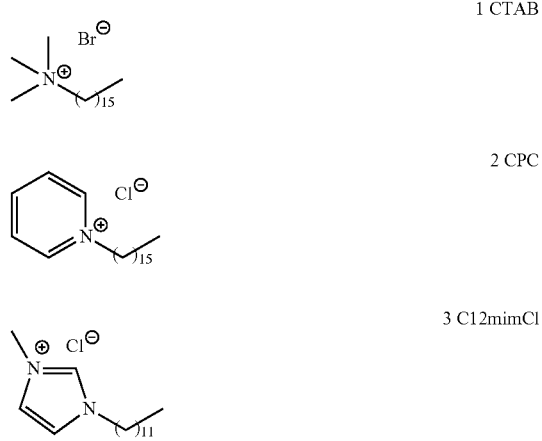

-continued

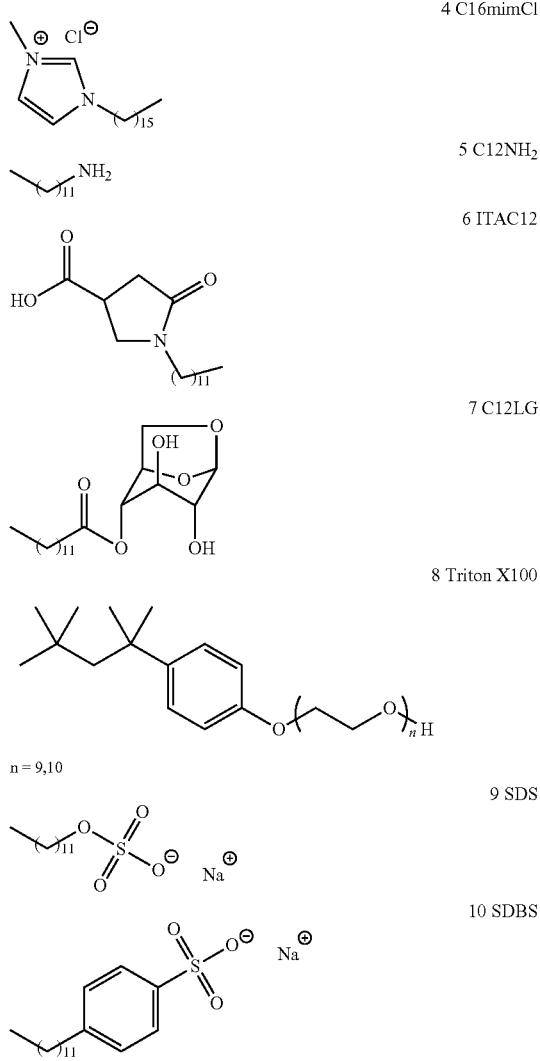

4 C16mimCl

5 C12NH2

6 ITAC12

7 C12LG

8 Triton X100
n = 9,10

9 SDS

10 SDBS

This choice of analytes was aimed to test a broad range of reagents and environmentally-sensitive solutes exhibiting different structures, charges, and functional units. Specifically, the examined compounds were nitrogen-, oxygen- and sulphur-containing molecules having the same chain lengths (twelve carbon atoms for compounds 3, 5, 6, 7, 9 and 10 and sixteen carbon atoms for compounds 1, 2 and 4) but displaying different charges (or no charges) in the polar head. Compounds 5, 6 and 7 can be considered as representative renewable surfactants, synthesized from renewable resources. Specifically, primary amines such as compound 5 are produced in industrial processes from lauric acid; 6 is obtained from the reaction of itaconic acid and dodecylamine 5. Itaconic acid is industrially obtained with high yields in biotechnical processes using substrates like sucrose, glucose, starch hydrolysates, or purified molasses and fungi of the genus *Aspergillus*. 7 is obtained through enzyme acylation of levoglucosan, a common anhydro-sugar, produced in high yields from the pyrolytic treatment of cellulose.

Scanned images of the color transformations induced by the analytes upon incubation with the PDA/PMMA, and PDA-NH$_2$/PDA/PMMA, were recorded after addition of the surfactants (concentrations 1 mM). Images were recorded after 40 minute incubation.

The choice of the two specific sensor compositions was aimed at assessing the effect of varying the PDA headgroup upon the chromatic properties and transformations. The obtained images clearly show that the surfactants induced distinct color changes upon incubation with the films. Furthermore, differences in color transitions are also apparent between films containing the two PDA derivatives.

Specifically, CTAB (1) induced a striking blue-yellow transformation upon incubation with the PDA/PMMA film, and yellow-orange color in case of PDA-NH$_2$/PDA/PMMA. In comparison, CPC (2) and the ILs displaying positively-charged bulky headgroups 3-4 gave rise to orange-red colors when added to PDA/PMMA, orange-purple shades upon addition to PDA-NH$_2$/PDA/PMMA. It appears that the difference in the length of the alkyl chains of ILs 3 and 4 (four carbon atoms) did not play a role in inducing color changes. While the ionic compounds 1-4 and the amine 5, which also is partially protonated in the experimental conditions, induced significant color changes, the carboxylate-type surfactant 6, the non-ionic surfactants 7-8 and anionic surfactants 9-10 produced small or insignificant color changes in the PDA/PMMA system, blue-purple transitions upon incubation with the PDA-NH$_2$/PDA/PMMA films (in case of the non-ionic surfactants).

Figure 3A:
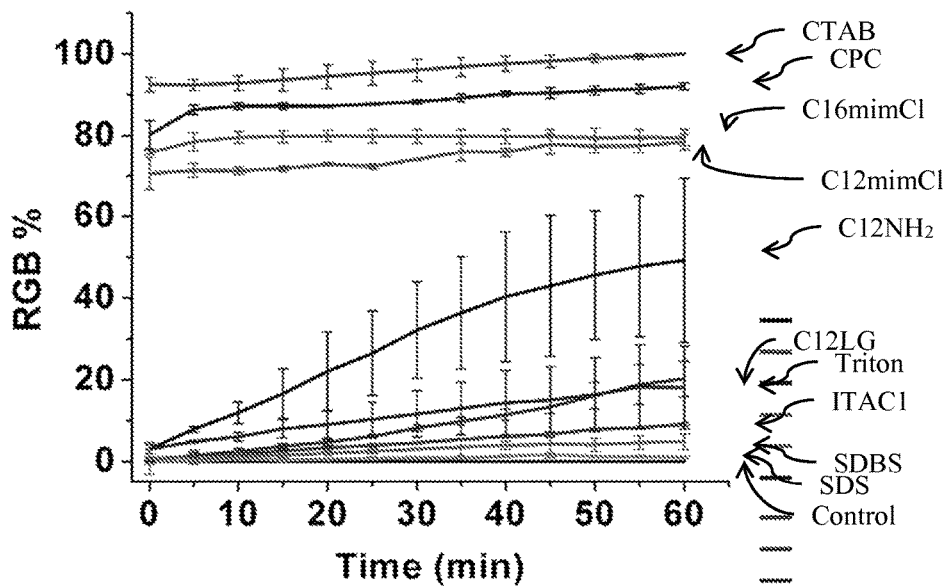
FIGS. 3A and 3B disclose time-dependent % RGB curves reflecting the extent of blue-red-yellow transformation of the PDA/PMMA film (A) and PDA-$NH_2$/PDA/PMMA film (B) after addition of amphiphilic compounds 1-10.
Figure 3B:
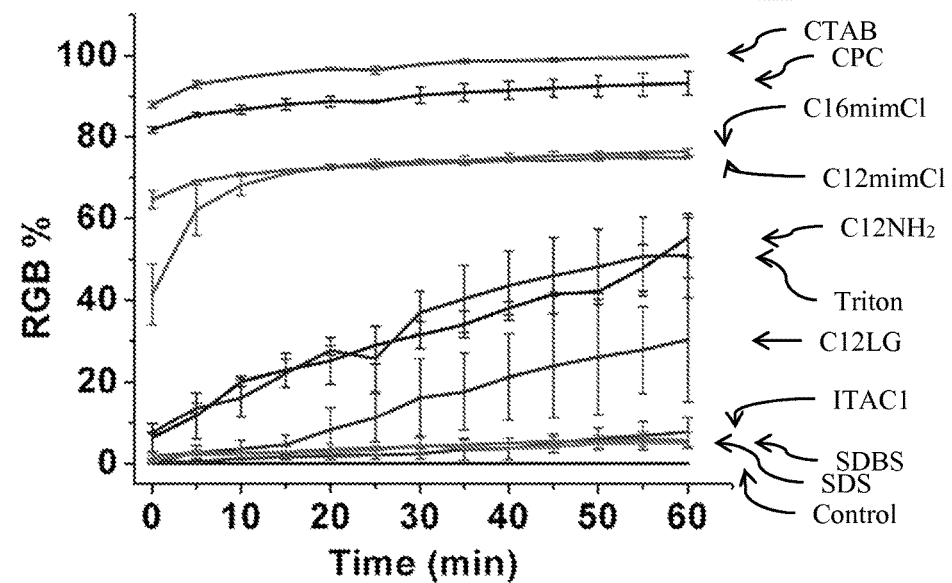

The kinetic curves in FIGS. 3A and 3B represent the extent of color transformations through combining image analysis of scanned images with summation of the red-blue-green components in each pixel. Essentially, the % RGB scale measures the blue-red-yellow transformations, in which high values correspond to the appearance of a yellow color, while lower % RGB reflects less pronounced color transitions (e.g. blue-purple and blue-red).

The % RGB analysis in FIGS. 3A and 3B underscores the significantly different color transformations both recorded among the compounds tested, and also between the two PDA film compositions. Specifically, high % RGB values were recorded when the cationic surfactants (1 and 2) or ILs (3 and 4) were added. These compounds furthermore induced almost instantaneous colorimetric transformations (FIGS. 3A and 3B). The non-ionic surfactants (7-8), on the other hand, gave rise to much lower % RGB values which gradually increased over time. This result likely reflects slow adsorption of these surfactants onto the PDA films. Note, however, that the % RGB graphs in FIGS. 3A and 3B clearly show that the non-ionic surfactants gave rise to greater color transformations upon addition to the PDA-NH2/PDA/PMMA films, reflecting the enhanced adsorption to the polar amine moieties. FIGS. 3A and 3B also demonstrate that the anionic surfactants 9-10 induced negligible color changes—ascribed to electrostatic repulsion to the PDA units that exhibit residual negative charge. A similar result was recorded in case of 6 which is anionic at the pH condition employed in the experiments (pH 8).

Interestingly, the % RGB curve recorded for dodecylamine (5) appears different than the other surfactants tested, initially inducing low % RGB values while rapidly increasing after few minutes. This distinct kinetic behavior is probably related to the much smaller headgroup of 5 as compared to the other surfactants examined, and/or to the presence of the basic nitrogen. Importantly, the quantitative kinetic analysis in FIGS. 3A and 3B underscores the differences between the chromatic responses of PDA/PMMA and PDA-NH2/PMMA: the ionic compounds induced higher % RGB when incubated with the (negatively-charged) carboxyl-displaying film, while the non-ionic surfactants generally gave rise to steeper % RGB kinetic curves in case of PDA-NH2/PDA/PMMA.

To shed light upon the colorimetric transitions induced by the surfactants in the PDA/PMMA films spectroscopic analyses were carried out (FIGS. 4A-4D).

Specifically, UV-vis spectra and fluorescence emission of representative films were recorded, together providing insight into the photophysical properties of the distinct PDA phases formed. The UV-vis spectra in FIGS. 4A-4B reveal that the yellow PDA phase (induced by incubation of the PDA/PMMA or PDA-NH2/PDA/PMMA films with CTAB) exhibits a distinct absorbance peak at ~500 nm. The red-orange PDA phase (shown is the UV-vis absorbance of the PDA/PMMA or PDA-NH2/PDA/PMMA following incubation with C12mimCl), however, displays the typical absorbance of red-phase PDA at around 540 nm, although the shoulder apparent in a lower wavelength suggests a contribution from the yellow PDA phase. The purple PDA/PMMA (induced by Triton X-100) gave rise to UV-vis spectra which either reflect incomplete blue-red transformation, or a mixture of the blue and red phases.

Figure 4A:
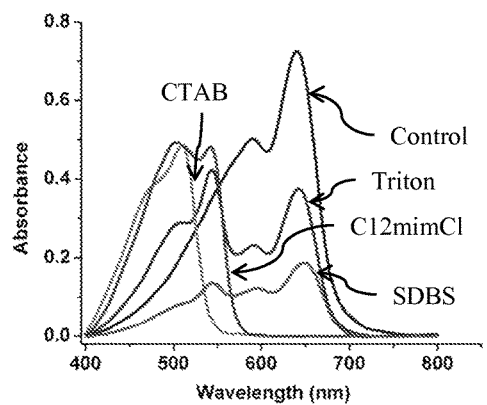
FIGS. 4A-4D disclose spectroscopic characterization of PMMA-supported PDA films undergoing distinct color transitions.
Figure 4B:
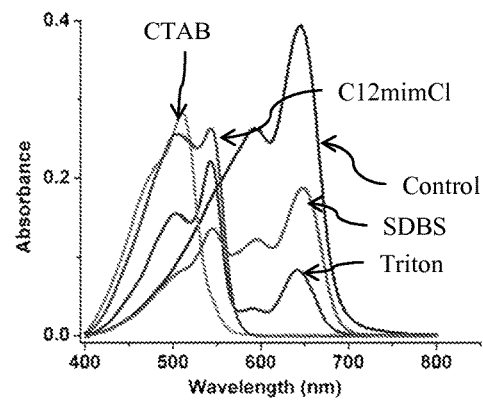
Figure 4C:
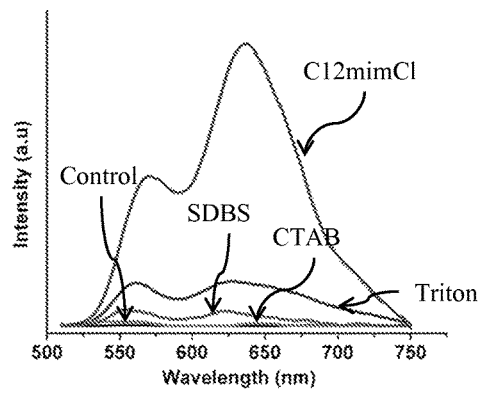
Figure 4D:
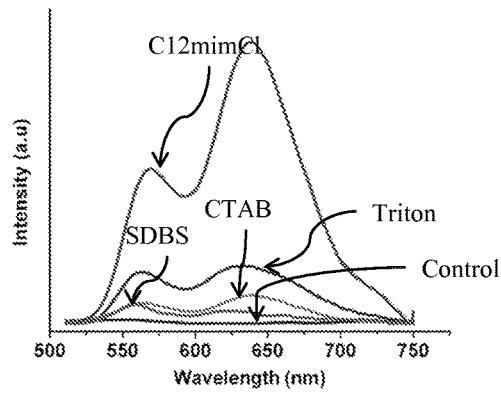

Dramatic differences between the analyte-induced chromatic transformations are apparent in the fluorescence emission spectra (excitation 482 nm, FIGS. 4C-4D). Surprisingly, the fluorescence spectra show that the yellow PDA film (following addition of CTAB) hardly exhibits fluorescence emission, similar to the non-fluorescent blue PDA. This observation, not reported previously, echoes the shifted visible absorbance peak recorded for the yellow PDA/PMMA films (FIGS. 4A-4B) and indicates that the yellow phase corresponds to a distinct PDA organization. In a sharp contrast, the red-phase PDA, formed through incubation of PDA/PMMA or PDA-NH2/PDA/PMMA with C12mimCl, was highly fluorescent (red curves in FIGS. 4C-4D), while the purple PDA/PMMA films (induced by Triton X-100) produced intermediate emission spectra. Together, the uv-vis and fluorescence emission data in FIGS. 4A-4D indicate that the dramatic color transitions recorded, i.e. blue-purple, blue-red, and blue-yellow (FIGS. 3A and 3B), are associated with formation of distinct PDA phases. Moreover, the spectroscopic data in FIGS. 4A-4D corroborate the colorimetric analysis above, and confirm that binding of molecules from each analyte family resulted in different structural/photophysical PDA transformations.

As noted hereiabove, more specific detection can be achieved by using a detector comprising one or more recognition elements.

Therefore, according to one preferred embodiment of the present invention, there is provided a method for detecting the presence of a specific analyte in a sample, comprising contacting the sample with the detector comprising a recognition element, wherein this recognition element has an affinity to the specific analyte.

In one such example, preliminary colorimetric experiments (FIG. 14) underscore the distinct color transformations induced by interactions between lanthanide ions and PDA matrices comprising different combinations of PDA, combined with TTA and BTOT which was used as recognition elements, upon a transparent Perspex substrate, as part of a specific detector as detailed above. The results have shown that different color changes were induced by specific ions, and have demonstrated the PDA film platform is capable of selectively distinguishing among different lanthanide ions and additional data indicates that the selectivity of the PDA system can be accomplished through incorporation of derivatized diacetylene receptors and tuning of the PDA matrix composition.

In another example, for the detection of oils, results were recorded for visual inspection (not provided herein), absorbance data (FIGS. 7-8), and fluorescence (FIGS. 10-11), and show that there is a distinct chromatic transformations (e.g. color and fluorescence transitions) associated with different PDA derivatives and different oil compounds.

Figure 7:
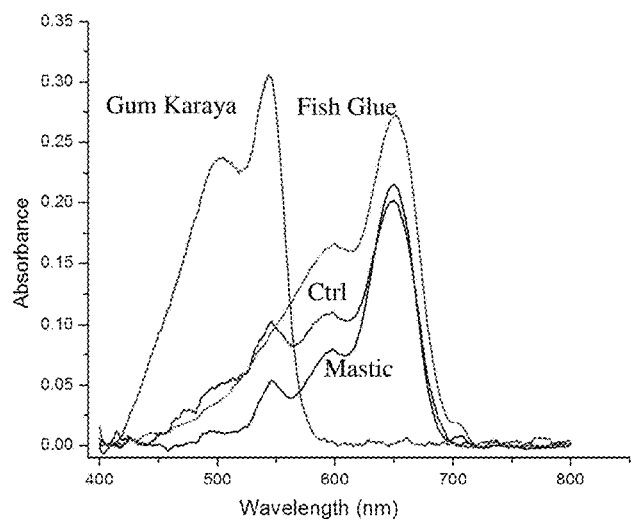
FIG. 7 discloses UV-vis absorption spectra of PDA after the addition of gums to films containing TRCDA coated on PMMA.

FIG. 7 discloses UV-vis absorption spectra of PDA after the addition of gums to films containing TRCDA coated on PMMA.

Figure 8:
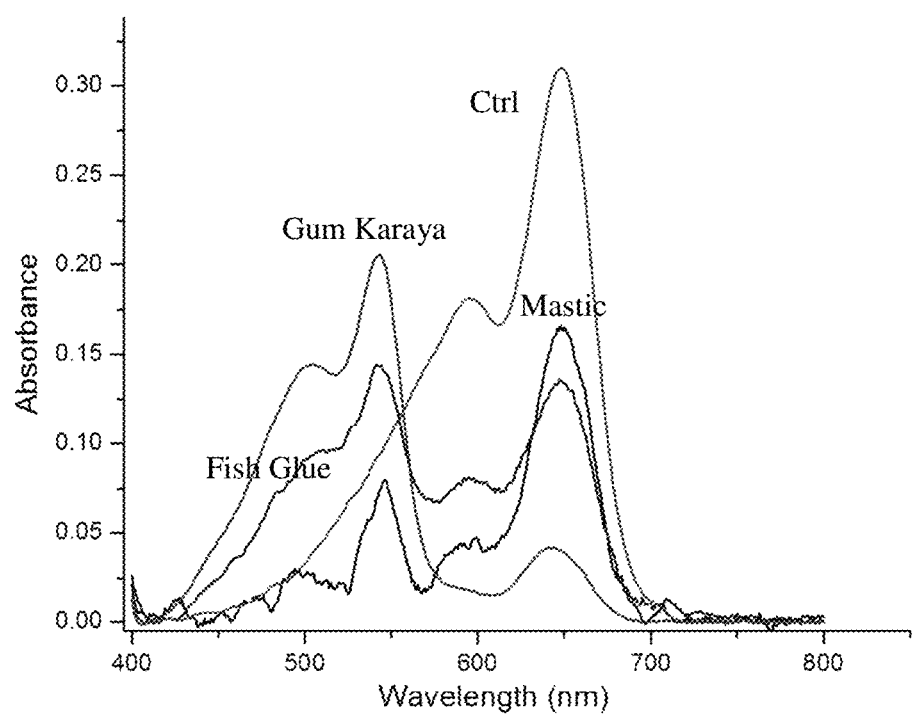
FIG. 8 discloses quantitative analysis of the color transitions for a PDA/PDA-F3 coated PMMA film. The CR percentage (% CR) is calculated as published elsewhere.

FIG. 8 discloses quantitative analysis of the color transitions for a PDA/PDA-F3 coated PMMA film. The CR percentage (% CR) is calculated as published elsewhere.

Figure 9A:
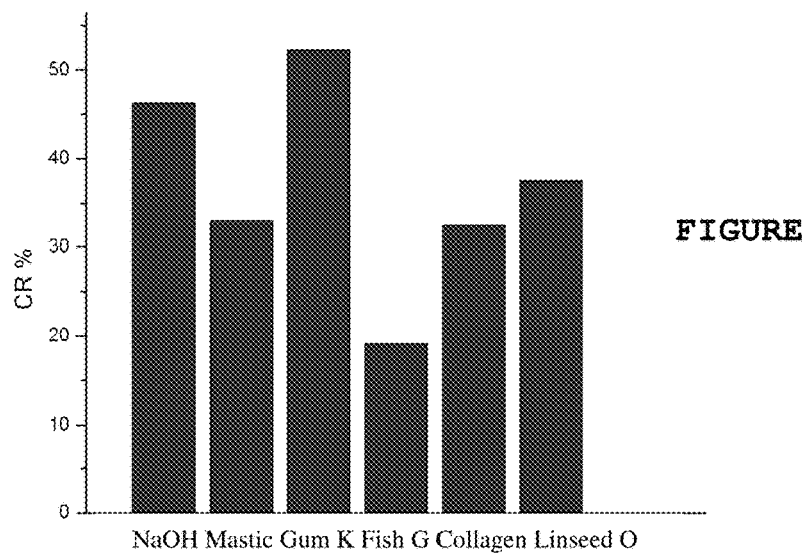
FIGS. 9A-9C show the % CR of after the addition of gums to films containing different PDA derivatives coating PMMA (FIG. 9B: PDA-NH2, FIG. 9C: PDA-F3, vs.
Figure 9B:
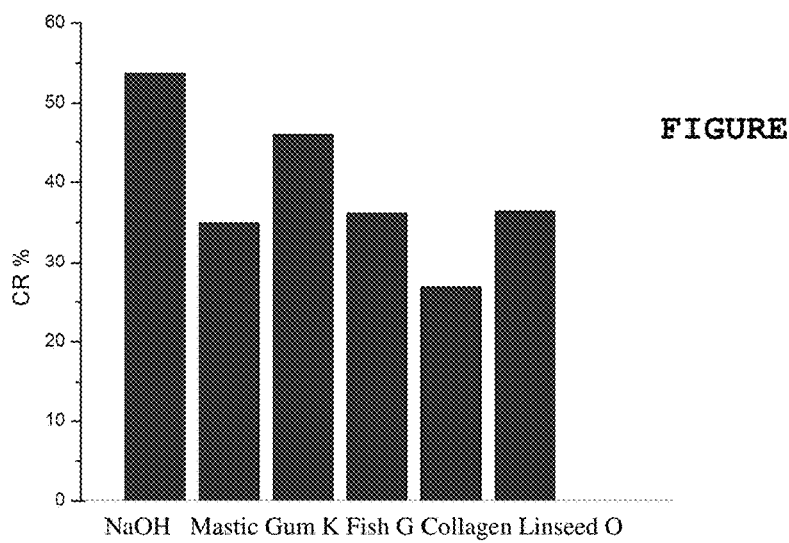
Figure 9C:
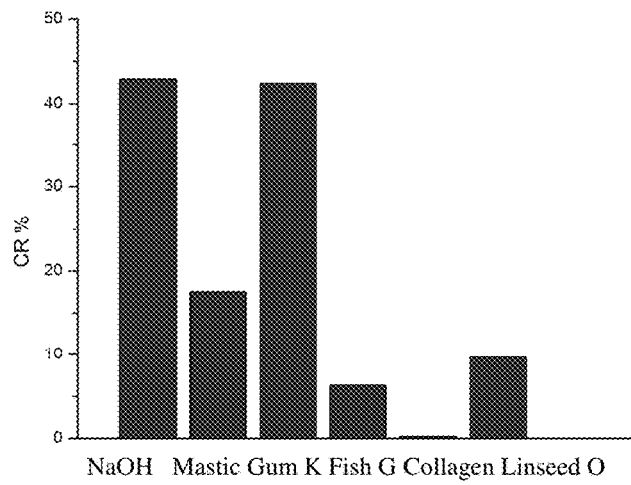

FIGS. 9A-9C show the % CR of after the addition of gums to films containing different PDA derivatives coating PMMA (FIG. 9B: PDA-NH2, FIG. 9C: PDA-F3, vs. FIG. 9A: unmodified PDA (TRCDA).

Figure 10A:
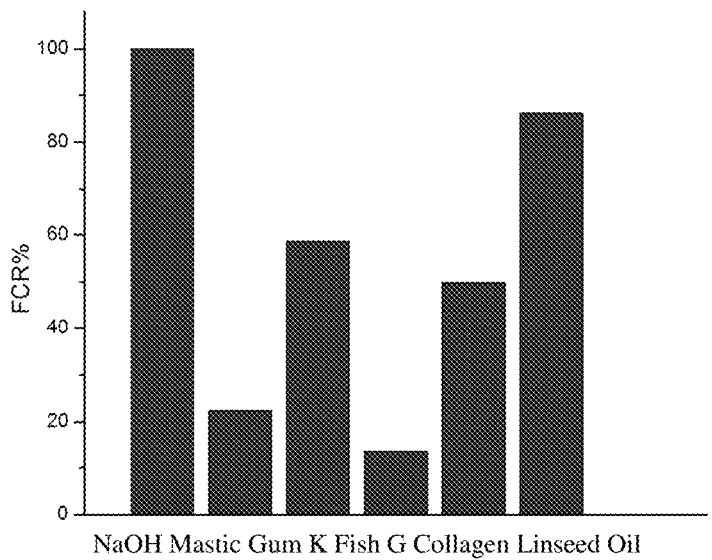
FIGS. 10A-10F show the % CR after the addition of gums to films containing different PDA derivatives deposited on PMMA (FIG. 10B: PDA/PDA-NH2, FIG. 10C: PDA/PDA-F3, FIG. 10D PDA/PDA-IF6.
Figure 10B:
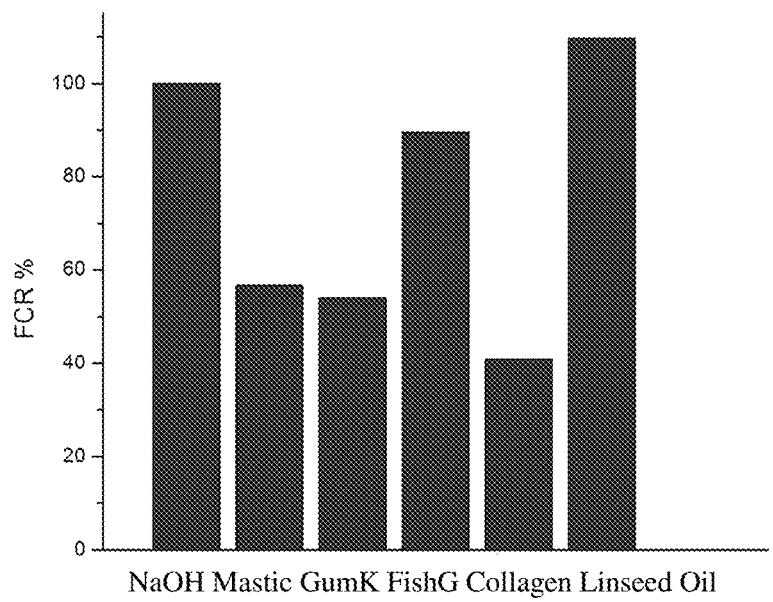
Figure 10C:
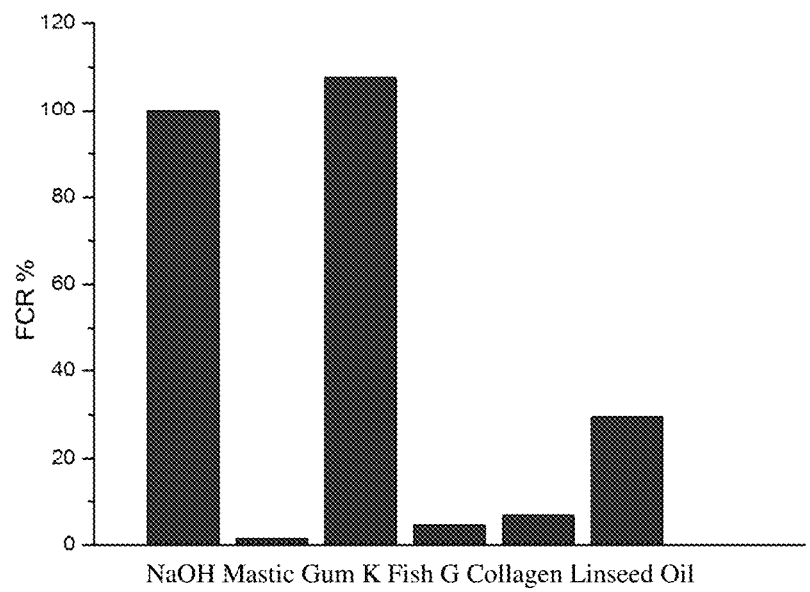
Figure 10D:
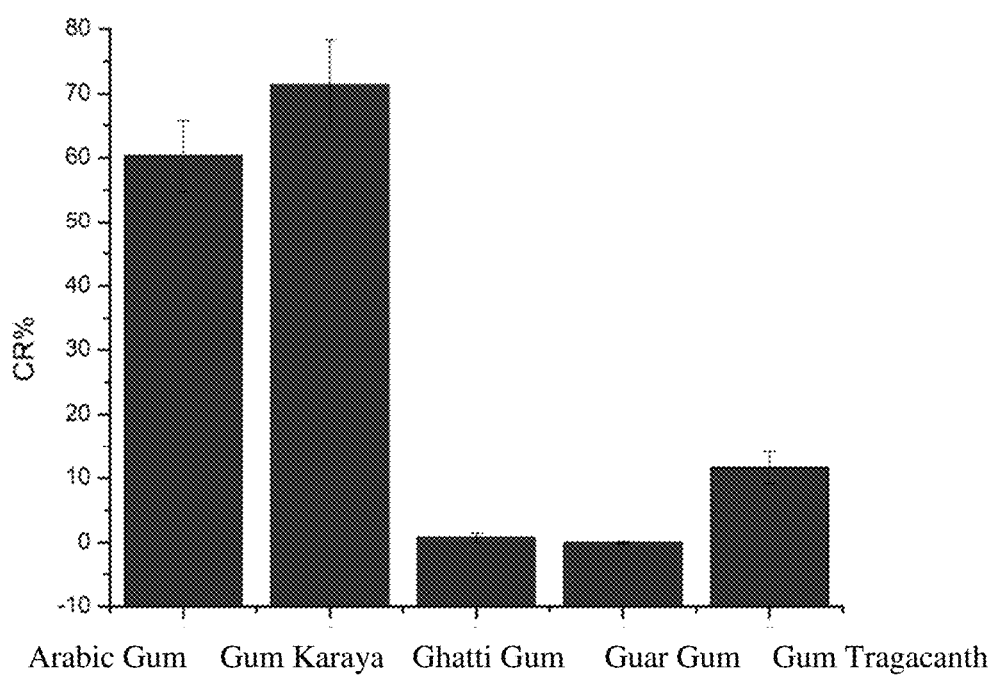
Figure 10E:
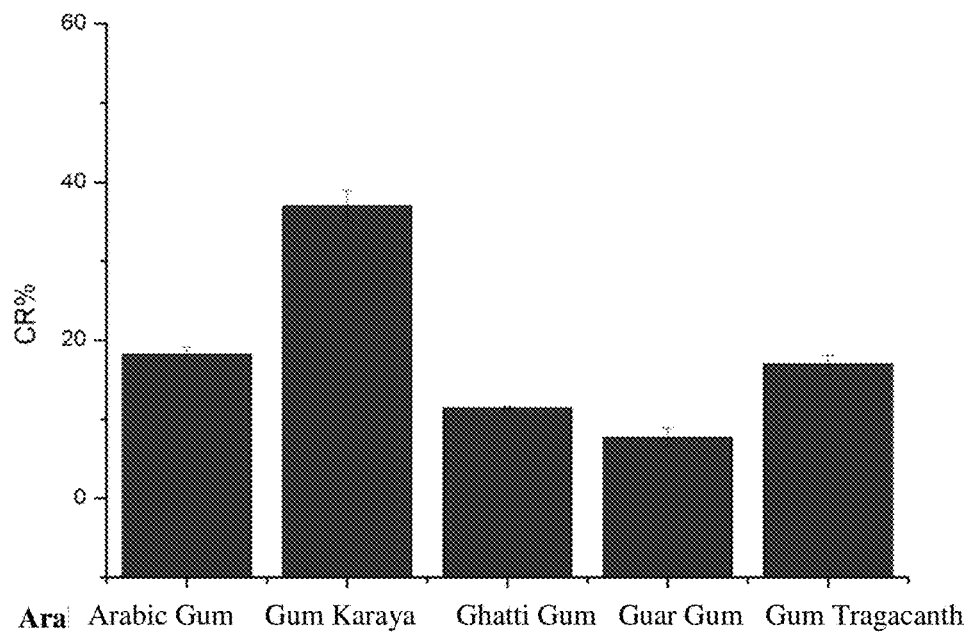
Figure 10F:
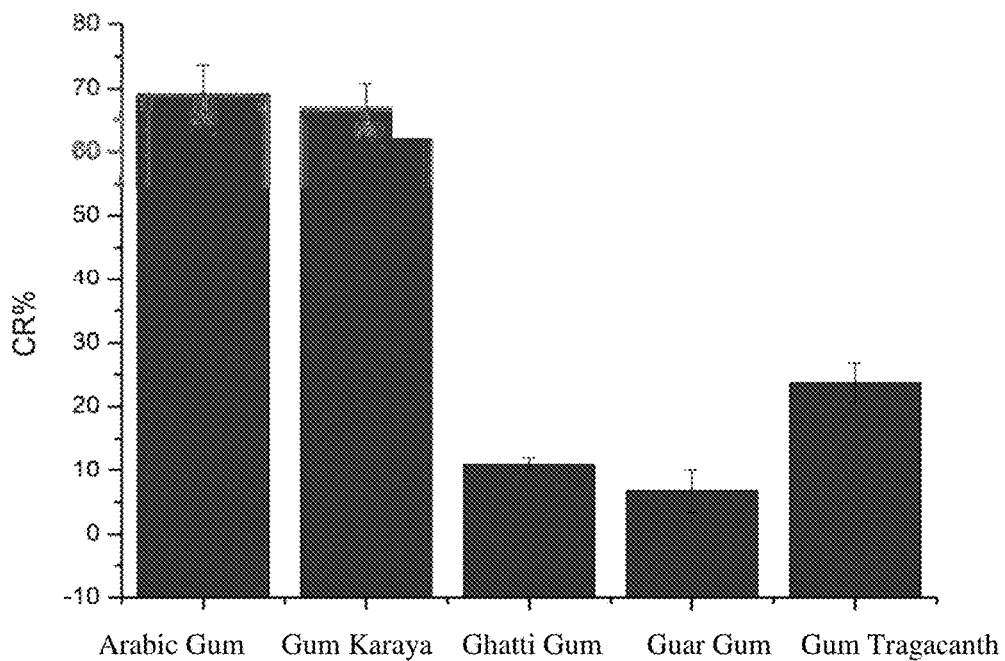

FIGS. 10A-10F show the % CR after the addition of gums to films containing different PDA derivatives deposited on PMMA (FIG. 10B: PDA/PDA-NH2, FIG. 10C: PDA/PDA-F3, FIG. 10D PDA/PDA-IF6; FIGS. 10A and 10E: PDA and FIG. 10F: PDA/PDA-PhB).

In yet another example, it has been shown that the addition of Monensin as a recognition element during the polymerization of the diacetylene monomer allowed the specific detection of ions in water. As a result of these specific interactions between the monensin ionophore and ions, more pronounced red absorbance and fluorescence emission (at 560 nm and 640 nm) were recorded in case of PDA/monensin films as compared to pure PDA films, in particular when detecting K+ and in particular for detecting Na+ ions to PDA/monensin.

One additional important aspect of the PDA/PMMA films of the present invention is the possibility for identifying analytes through colorimetric fingerprinting—basically using different PDA derivatives and having "color patterns" (i.e. "fingerprint") for each compound.

This is done by determining the sensitivities of a given PDA to a given analyte in order to generate identifiable fingerprints characteristic of each analyte.

As an example, say that the PDA derivative "A" on PMMA may convert completely to an red phase in the presence of a tested analyte (% CR=100), while the PDA derivative "B" on PMMA may have a % CR of 70 giving rise to a pink color, while the PDA derivative "C" on PMMA may have a % CR of 40 yielding a purple color and the PDA derivative "D" on PMMA may not change at all (i.e., therefore, remains blue/purple). The response fingerprint orange/pink/purple/blue-purple would indicate the presence of the analyte.

Clearly, the higher the number of elements in the array, the greater the chance of a positive identification for a given analyte. The use of PDA films on the PMMA surface is simple, and therefore the generation of such arrays, of any desired size and shape can be created and incorporated into a small, easily read and interpretable device.

In one such example, the fingerprinting method is used for the sensing/distinguishing of different oils, such as found in paintings and artwork.

In another example, the fingerprinting method is used for the detection of pollutants in water, such as for the specific detetion of pesticides.

Figure 15:
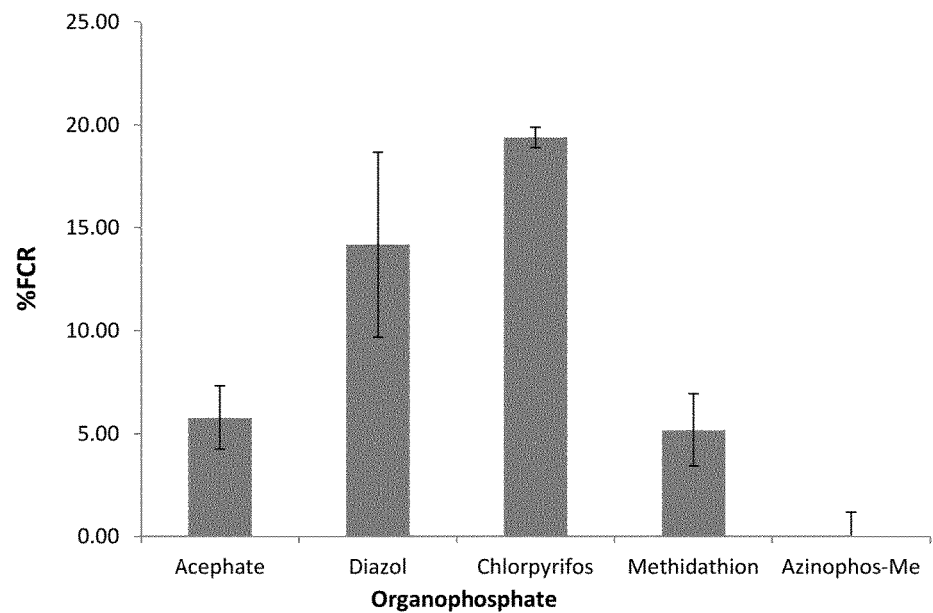
FIGS. 15A-C represent fluorescent spectrum of the blue film (before addition of milk, or upon addition of the control milk) and red film.
Figure 15:
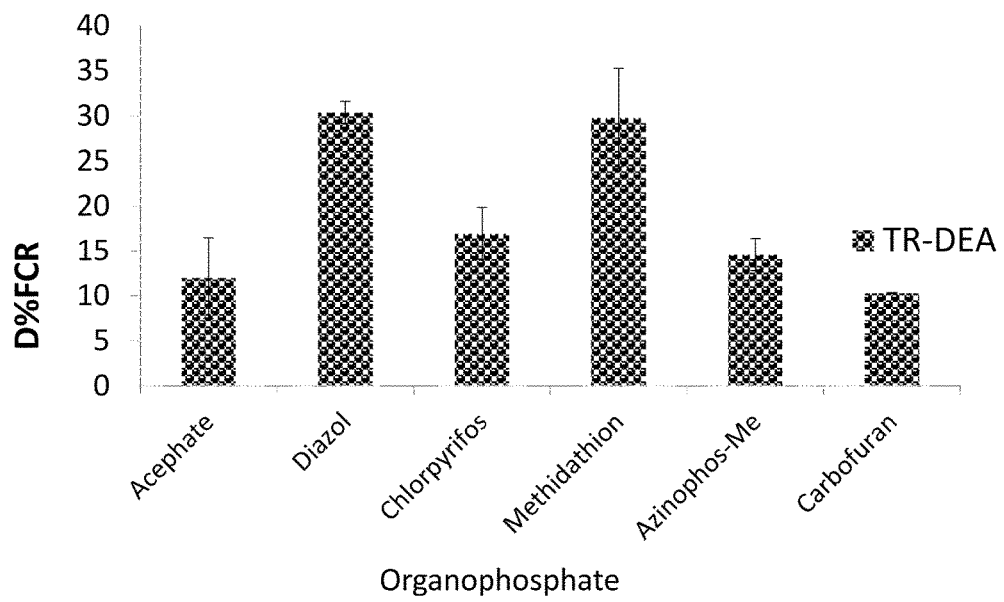
Figure 15:
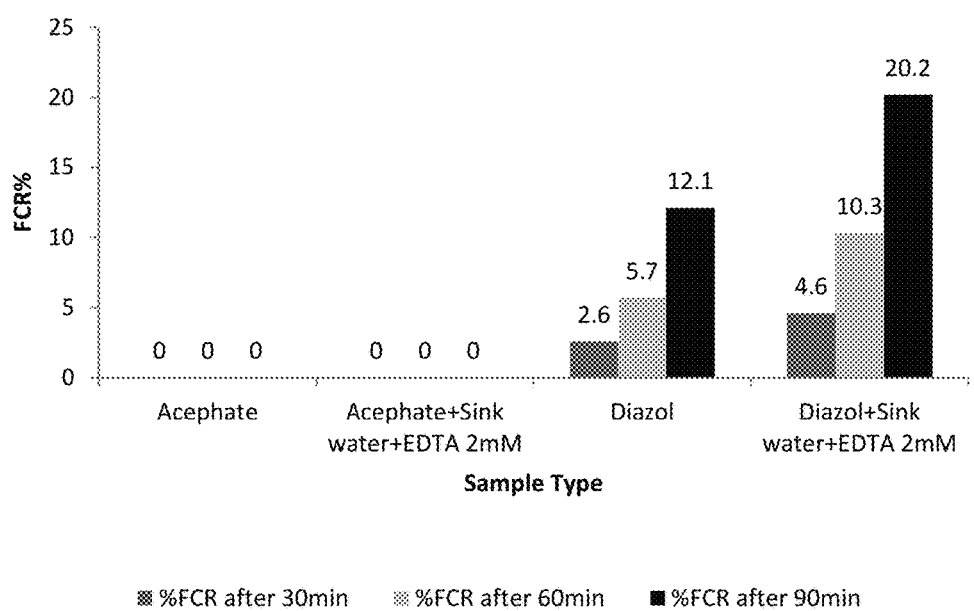

It can be seen in FIGS. 15A-15C that different chromatic responses were recorded for a variety of organophosphate pesticides.

For example,

FIG. 15A discloses different organophosphate on TRCDA/TR-NaPh 1:1 ratio, after 90 minutes;

FIG. 15B discloses the same organophosphate on a PDA/TR-DEA detector 1:1 ratio after 15 minutes;

FIG. 15C: discloses the same organophosphate on a PDA/TR-MPhe detector

Thus, according to one specific embodiment of the present invention, there is now provided a fingerprinting detection method of analytes in a sample, this method comprising contacting at least four separate samples of the analyte with at least five different polydiacetylene matrices, and letting the samples incubate for an incubation time ranging from 10 seconds to about 3 hours, preferably for less than 60 minutes and even less than 20 minutes; measuring the color change and/or fluorescence thereof and creating a colorimetric and/or fluorescent fingerprint portfolio of the analyte.

As detailed hereinabove, this method was successfully used for the fingerprinting detection of oils in water.

In another example, this method was successfully used for the fingerprinting detection of pesticides in water.

It should be noted that using a detector wherein the PDA comprises at least 40 molar percent of polymerized units of a diacetylene monomer having small and hydrophilic head group, as taught hereinabove, increases the detection sensitivity towards ionic analytes.

Therefore, according to one preferred embodiment of the present invention, there is provided a method for detecting the presence of an ionic analyte in a sample, this method comprising contacting the sample with the detector having a PDA comprising at least 40 molar percent of polymerized units of a diacetylene monomer having hydrophilic head group, which comprise up to 5 atoms.

As clear from the above descriptions, according to yet another aspect of the present invention, there is now provided the use of the colorimetric and/or fluorescent detector described herein for the detection of the presence of analytes in a sample.

In one preferred embodiment, there is provided the use of this detector for the detection of subclinical-to-clinical SCC levels in cows.

In another preferred embodiment, there is provided the use of this detector for the detection of surfactants and/or ions and/or metals and/or pollutants in water.

In another preferred embodiment, there is provided the use of this detector for the detection of pesticides in water.

As taught in the experimental section which follows, the present invention teaches the preparation of a large number of PDA/PMMA detector systems.

Thus, according to another aspect of the invention, there is provided a method for preparing colorimetric and/or fluorescent detector, this method comprising depositing at least one diacetylene monomers upon a PMMA substrate, followed by UV irradiation thereof.

It should once more be clarified, that a large number of diacetylene monomer can be used as part of the present invention, and while the preparation of some has been disclosed in details in the experimental section below, it is impossible to provide preparation methods to all of the possible monomers, nor is it possible to limit the diacetylene monomers to those listed and exemplified below, since any number of modifications may be suggested and developed, either now or in the future, depending on specific detection needs, samples and analytes to be tested.

As detailed in the experimental section hereinbelow, the monomers are prepared in a solution, and are mixed in solution with any other monomers, recognition elements and/or additives.

Suitable solvents are exemplified below, and are further common knowledge in the field, depending on the character of the solvated monomers and/or recognition elements and/or additives.

As used herein the term "coating" and the term "depositing" are used synonymously and refer to a process of placing or applying a substance onto another substance, in the present case-applying the diacetylene monomeric solution on a PMMA surface.

Depositing may include, but is not limited to, methods of using spraying, dip casting, spin coating, evaporative methods, sputter methods, immersion methods, extractive deposition methods, or other methods to associate the items or substances. The term depositing includes applying the item or substance to substantially the entire surface as well as applying the item or substance to a portion of the surface.

One possible way to deposit the diacetylene monomers on the PMMA substrate is by dip coating.

The term "dip coating" is used to denote coating a substrate involving translational symmetry by dipping same into a material, pulling it out at a constant speed so that a liquid film remains clinging to the substrate surface, and drying thereof.

According to one preferred embodiment of the invention, the diacetylene monomers are applied onto the PMMA substrate by spin-coating.

The term "spin coating" is used to denote the application of a uniformly thin film to a flat rotationally symmetrical substrate by the distribution of a material under centrifugal force with rapid rotation of the substrate.

A typical "spin coating" process involves depositing a small puddle of a fluid material onto the center of a substrate and then spinning the substrate at high speed (typically around 3000 rpm). Centripetal acceleration will cause most of the resin to spread to, and eventually off, the edge of the substrate, leaving a thin film of material on the surface. The final film thickness and other properties will depend on the properties of the fluid material (in this case the diacetylene monomer solution, including any additives and/or recognition elements) and the parameters chosen for the spin process.

After dispensing the monomer solution a relatively high speed is used to thin the fluid. Typical spin speeds for this step range from 1500-6000 rpm. This step can take from 10 seconds to several minutes.

The combination of spin speed and time selected for this step will generally define the final film thickness.

A separate drying step is sometimes added after the high speed spin step to further dry the film without substantially thinning it.

In one preferred embodiment, the spin-coating is conducted at 1500-2500 rpm for about 30 seconds.

Following depositing the monomeric solution on the PMMA, as described herein, an irradiation step takes place.

The irradiation step is intended to cure or polymerize the diacetylene monomers.

Therefore, the term "irradiating" as used herein, refers to exposing a surface to a radiation source which can produce polymerization reactions, such as, by way of example only, ultraviolet radiation. This may include polymerization by any light, such as sunlight, which contains UV components.

The term "UV radiation" in the context of this invention is intended to mean electromagnetic radiation in a wavelength range of from 200 to 400 nm.

According to another preferred embodiment of the invention, the irradiation is conducted at a wave length of 254 nm.

At this wave length, and for the diacetylene monomers exemplified below, the irradiation time was relatively short, and was often less than 2 minutes.

According to one preferred embodiment of the invention, the irradiation is conducted for a time ranging from 0.3 to 1 minutes.

Sometimes, it may be desired to enhance the polymerization by the addition of polymerization initiators, in particular photo initiators.

As used herein, the term "photo-initiators" refers to compounds that absorb ultra-violet light and use the energy of that light to promote the formation of a dry layer of coating. Photo-initiators may promote the reaction of monomers with each other and thus aid in the polymerization process.

As noted hereinabove, preferably at least 40 molar percent of the diacetylene monomers have a small and hydrophilic head group, therefore according to one preferred embodiment, the method comprises depositing upon a PMMA substrate one or more diacetylene monomers, followed by UV irradiation, wherein at least 40 molar percent of the one or more diacetylene monomers have a hydrophilic head group, further wherein this head group comprises up to 5 atoms.

As further noted hereinabove, the diacetylene monomers may be advantageously combined with one or more recognition elements.

Therefore, according to anther preferred embodiment, the method comprises depositing upon a PMMA substrate one or more diacetylene monomers, in the presence of one or more recognition elements, followed by UV irradiation.

As noted hereinabove, the diacetylene monomers are deposited on a PMMA surface.

The terms "surface", "solid support", "support structure", and "substrate" as used herein are used interchangeably and refer to a polymethylmetacrylate (PMMA) rigid or semi-rigid surface or surfaces.

There is no limitation to the shape or size of the support structures. In many embodiments, the solid support(s) will take the form of planar plates, beads, resins, gels, microspheres, or other geometric configurations.

According to one preferred embodiment, the PMMA surface is a PMMA planar surface.

As used herein, the term "planar surface" refers to a generally two-dimensional structure on a solid substrate, which is usually, but not necessarily, rigid and not necessarily flat. In particular, the term "planar surface" as used herein is meant to encompass flat as well as curved surfaces of PMMA.

However, as apparent to a person skilled in the art, the PMMA substrate can also be composed of surfaces that are not planar.

Thus, according to one preferred embodiment, the PMMA substrate is a non-planar surface.

The term "non-planar" surface refers to a surface or article having a continuous, intermittent, unidirectional or compound curvature.

Beads are an example of a non-planar surface.

PDA-coated beads might exhibit better detection sensitivity and high stability for long term use. Another potential advantage is to achieve analyte specificity through displaying different TR units on beads having different sizes, and subsequently resolving fluorescence/colorimetric signals through size fractioning [akin to fluorescence activated cell sorting, FACS].

Thus, according to another preferred embodiment, the PMMA non-planar substrate is a PMMA bead. In particular, the PDA substrate may be a multiplicity of PMMA beads, whereas the beads may have different diameters.

As explained in detail hereinabove, a large number of diacetylene monomers may be used for the purpose of the present invention, and depending on the analyte to be tested, there can be many optional derivatizations thereof, to include head groups that have an affinity to the tested analyte.

Therefore, it is impossible to describe all the possible combinations of alternative head groups and/or recognition elements with the diacetylene monomers that can be used to prepare new colorimetric and/or fluorescent detectors according to the present invention, as would be understood by any person skilled in the art.

As a general guideline for the selection of suitable recognition elements as head group for the diacetylene monomers for the development of new PDA/PMMA detectors of a given analyte, one would take the following steps:

a) Choose a diacetylene monomer to serve as a basic unit that can later be derivatized. Preferably this would be a diacetylene monomer having a small and hydrophilic head group as described hereinabove.

b) Select from about 10 to 20 molecular recognition elements that can potentially serve as recognition element head groups of diacetylene monomers, by selecting those that have a similar structure or some other affinity to the analyte to be detected;

c) Use conventional chemistry to prepare diacetylene monomers that incorporate the afore mentioned head groups;

d) Separately polymerize on a PMMA substrate an exemplary 1:1 mole mixture of the "base" diacetylene monomer, preferably one that has a small and hydrophilic head group, with the modified diacetylene monomers prepared in the previous step to create a detector film, comprising an array of several polymerized diacetylenes on the PMMA substrate;

e) Conduct an initial screening of the detector films obtained in the previous step, by separately adding the analyte to the different films, and choosing the films which exhibited the most pronounced color change (preferred films);

f) Preparing a $2^{nd}$ set of PDA films on PMMA, using the preferred films of the previous step, while varying the mole ratio between the "basic" and modified diacetylene monomers, ranging from 10% to 60% of the modified monomers, to obtain the recommended ratios of the preferred films; and optionally g) Adding non-polymeric additives to increase some of the properties of the detector or of the polymerization.

Alternatively, the recognition elements may be added without them being covalently attached to the diacetylene monomer. In this case, as a general guideline, for the development of new PDA/PMMA detectors of a given analyte, one would take the following steps:

a) Choose a diacetylene monomer to serve as a basic monomeric unit. Preferably this would be a diacetylene monomer having a small and hydrophilic head group as described hereinabove.

b) Select from about 10 to 20 molecular recognition elements that can potentially serve as recognition elements, by selecting those that have a similar structure or some other affinity to the analyte to be detected;

c) Separately polymerize on a PMMA substrate the diacetylene monomer chosen in step a, preferably one that has a small and hydrophilic head group, in the presence of different recognition elemets selected in the previous step to create a detector film, comprising an array of polymerized diacetylenes blended with rrecignition elements, on the PMMA substrate;

d) Conduct an initial screening of the detector films obtained in the previous step, by separately adding the analyte to the different films, and choosing the films which exhibited the most pronounced color change (preferred films);

e) Preparing a $2^{nd}$ set of PDA films on PMMA, using the preferred films of the previous step, while varying the mole ratio between the "basic" diacetylene monomers and the recognition element, ranging from 10% to 60% of the recognition element, to obtain the recommended ratios of the preferred films; and optionally f) Adding non-polymeric additives to increase some of the properties of the detector or of the polymerization.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials

The diacetylene monomer 10,12-tricosadiynoic acid (TRCDA) and 1-hexadecyltrimethylammonium bromide (CTAB) were purchased from Alfa Aesar;

Poly(methyl methacrylate) (PMMA, or Perspex) was purchased from Segalovitch Israel;

Tetrahydrofuran (THF) and diethyl ether were purchased from Bio-Lab Ltd;

Dichloromethane (DCM), ammonium hydroxide, chloroform ($CHCl_3$) and methanol were purchased from Frutarom Ltd;

Monensin, phosphatydilethanoleamine (PE) and all other chemicals were purchased from Sigma Aldrich.

All the reagents and solvents were used as received without further purification, unless taught otherwise.

General Procedures and Instruments

Bacteria Growth: Bacteria were grown in 10 mL Luria-Bertani (LB) growth media until saturation: $10^7$ cells/mL were used in the experiments.

Spin-coating was conducted at 1500-2500 rpm for about 30 seconds using WS-650 LITE spin coater (Laurell Technologies Corporation, USA).

Synthesis of Analytes and Starting Materials

Preparation of Ionic Liquids (ILs):
3: 1-dodecyl-3-methylimidazolium chloride, C12mimCl and 4: 1-hexadecyl-3-methylimidazolium chloride, C16mimCl (the numbers refer to the compounds outlined in Scheme 1, below): ILs 3 and 4 were synthesized according to the procedure reported in the literature[32] by mixing 1-methylimidazole (1 equivalent) with the corresponding chloroalkane (C12 or C16, 1.1 equivalent) at 50° C. After 24 hours the ILs were washed with diethyl ether (×2) and ethyl acetate (×2) to remove unreacted reagents. After solvent separation the solvent residue was evaporated under reduced pressure. ILs synthesized were dissolved in a small volume of acetonitrile and passed through a thin column of activated charcoal and silica gel to exclude the presence of colored impurities often present in ILs.

6: 1-lauryl-4-carboxy-2-pyrrolidone, ITAC12 was synthesized under solventless conditions through adapting a published procedure (Galletti, P. et al., Enzymatic Acylation of Levoglucosan in Acetonitrile and Ionic Liquids. Green Chem. 2007, 9, 987-991): Briefly, dodecylamine (1 equivalent) was added to a two necked round-bottom flask and heated at 40° C. for few minutes until complete melting. Itaconic acid (1 equivalent) was added to dodecylamine and the mixture heated at 100° C. for 3 hours. The reaction was monitored by thin layer chromatography (TLC) (cyclohexane: ethyl acetate=2:8). The product was purified using column chromatography (cyclohexane/ethyl acetate, gradient elution).

7: 4-O-Lauryl-levoglucosan, C12LG was synthesized and purified from levoglucosan and lauric acid by Lipase catalyzed esterification following published procedure (Volinsky, R. et al., Glass-Supported Lipid/Polydiacetylene Films for Colour Sensing of Membrane-Active Compounds. Biosens. Bioelectron. 2007, 22, 3247-3251).

The synthesis of 1,10-bis(thiophene-2'-yl)-4,4,5,5,6,6,7,7-octafluorodecane-1,3,8,10-tetraone (BTOT), was conducted by a collaborating laboratory.

Preparation of Pesticide Solutions:
Experiments were conducted with different sample pesticides (Organo phosphorus, OP) in water. OPs that were tested were: Acephate, Diazol (Diazinon), Chlorpyrifos, Methidathion, Azinophos-Methyl Preparation of Organo Phosphate (OP) 100 Ppm Solutions:
Fresh OP solution were prepared before each experiment. Each OP was dissolved according to the following steps to get final concentration of 100 ppm:
Step 1—2000 ppm solution: 2 mg OP dissolved in 1000 L Trifluoroethanol (TFE)
Step 2—1000 ppm solution: 200 L solution 2000 ppm+200 L TFE
Step 3—100 ppm solution: 30 L solution 1000 ppm+270 L DI water All of the Step 3 solutions were sonicated for at least 5 minutes and the next step was immediately conducted.

Mixing of OP Solutions into Tris Buffer for 50 Ppm and 20 Ppm Concentration:
Freshly prepared 40 mM Tris buffer (150 μL at pH=8.0) was transferred into a 4 mL clean vial. The previously prepared sample solution vial was opened and vortexed for a few seconds at the lowest possible speed, and the OP 100 ppm solution (150 μL) was immediately transferred into the 4 mL vial that contains the Tris buffer. These mixed solutions were later dropped over the PDA films. The solution was further diluted to obtain a 20 ppm, 10 ppm and 1 ppm solutions.

Analytical Methods

Quantitative Color Analysis.
Quantification of the color transitions was based upon a published procedure for RGB analysis of PDA films: "Glass-Supported Lipid/Polydiacetylene Films for Color Sensing of Membrane-Active Compounds" R. Volinsky, S. Kolusheva, T. Sheynis, M. Kliger, R. Jelinek, *Biosensors & Bioelectronics*, 2007, 22, 3247-3251).

Briefly, 48-well plates containing the spin-coated PMMA-supported PDA films incubated with the amphiphilic compounds were scanned in the transmitted mode on an Epson 4990 Photo scanner to produce 2400 dpi, 24 bit color depth red-green-blue (RGB) images. Digital colorimetric analysis (DCA) was carried out by extracting RGB channel values for each pixel within the sample spots in the scanned images, and the color change values were calculated using Matlab R2010 scientific software (The Mathworks, Inc., MA, USA) as detailed previously (Volinsky et al, 2007). No major changes were made to the program, which allowed us to calculate color change from the blue to yellow phases. DCA utilizes the standard "red-green-blue" (sRGB) model translating color signals into three distinct values corresponding to the intensities of red (R), green (G), and blue (B) color channels. Accordingly, the relative intensity of a particular RGB component in a scanned image can be defined as the chromaticity level. For example, the yellow chromaticity level (y) in each pixel was calculated as:

$$y=(R+G)/(R+G+B);$$

where R (red), G (green), and B (blue) are the three primary color components. For a defined surface area within a PDA-based sensor well a quantitative parameter was defined and denoted "yellow chromaticity shift" (YCS). This parameter represents the blue-red and blue-red-yellow transformations of the pixels in the analyzed film area:

$$YCS=(y_{sample}-y_0)/(y_{max}-y_0)\times 100\%$$

where $y_{sample}$ is the average yellow chromaticity level of all pixels in the scanned surface, $y_0$ is the average yellow level calculated in a blank surface (blue PDA film) and $y_{max}$ is the average yellow chromaticity level of the maximal blue-yellow transition occurring at the PDA film. In essence, YCS is the normalized change in the chromaticity level within the sensor well surface on which the tested sample was deposited.

UV-Vis Spectroscopy. UV-Vis spectroscopy measurements were carried out at 23° C. on a Varioskan (Thermo, Finland).

Fluorescence Spectroscopy. 48 well plates containing the PMMA-coated PDA films were placed in a multiwall fluorescence plate reader (Varioskan, Thermo, Finland) at 23° C. All measurements were carried out using 482 nm excitation. The curves obtained were smoothed by using a 10 point adjacent averaging.

Multiwell Fluorescence Spectroscopy

A quantitative value for the extent of the blue-to-red color transitions is given by the fluorescence colorimetric response (% FCR), which is defined as follows:

$$\% FCR=[(F_1-F_0)/F_{100}]\times 100$$

where F1 is the fluorescence measurement of the vesicles after the addition of the compounds, $F_0$ is the fluorescence of the control sample (without addition of the compounds) and $F_{100}$ is the fluorescence of a positive control sample (heated to produce the highest fluorescence emission of the red PDA phase). Integration Time was 40 ms, Excitation is at 485 nm and Emission is at 555 nm, Beam was set to Normal.

Raman Scattering. Raman spectra were recorded with a Jobin-Yvon LabRam HR 800 micro-Raman system, equipped with a liquid-$N_2$-cooled detector. The excitation source was an Argon laser (514 nm), with a power of 5 mW on the sample. In order to protect the samples the laser power was reduced by 1000 using ND filters. The laser was focused with 100× long-focal-length objective to a spot of about 4 µm. Measurements were taken with the 600 g mm$^{-1}$ grating and a confocal microscope with a 100 µm hole with a typical exposure time of 1 min.

Scanning Electron Microscopy (SEM). Scanning electron microscopy (SEM) images were recorded on a JEOL JSM-7400F (Tokyo, Japan) Scanning Electron Microscope. Images were taken after sputtering a thin film of Au (~15 nm thickness) over the substrates for better contrast and minimum charging.

EXPERIMENTAL RESULTS

Example 1

Preparation of Diacetylene Monomers

Preparation of Filtered TRCDA: 10,12-tricosadiynoic acid (TRCDA, 0.2 grams) was weighted into a clean 20 mL veil and Chloroform (5 mL) was added. The solution was filtered through 0.22 µm PTFE syringe filter (or other compatible materials like nylon) into a new 20 mL veil. Chloroform was evaporated until a dry white powder was formed.

Preparation of PDAs Having an Amine Head Group

Several compounds having an amine head group were prepared, including, but not limited to: 10,12-diynamine (TRCDA-amine or TR-TEA) or N-(2-aminoethyl)docosa-10,12-diynamide (TR-EDA), 2-(docosa-10,12-diynamido)-N,N,N-trimethylethanaminium (TR-TDEA or TR-N3), methyl 6-amino-2-(docosa-10,12-diynamido)hexanoate (TR-MLys).

For example, the synthesis of 10,12-tricosadiyn amine (TRCDA-amine)—was carried out through a two-step pathway:

(i) TRCDA (570 mg) was dissolved in DCM (20 mL). 2 mL of oxalyl chloride is added to the solution under argon atmosphere. Several drops of DMF were then added as catalyst. The mixture is stirred at room temperature for overnight. After this, the solvent was evaporated and the residue was dissolved in dry THF (20 mL). The solution was then slowly added to 30 mL ammonium hydroxide (25%) in an ice bath and stirred overnight. The solvent was evaporated and the residue was extracted with DCM three times. The organic layer was dried over $MgSO_4$, filtered and evaporated to dryness.

ii) The residue obtained in the first step was added to 30 mL diethyl ether. $LiAkH_4$ (550 mg) was added to it while keeping the solution in an ice bath (caution: it is essential to avoid dropping $LiAlH_4$ powder into ice, which causes violent reaction). The solution was stirred overnight and then poured into a saturated solution of $NH_4Cl$. The aqueous layer was then extracted with ethyl acetate. The combined organic layer was washed with saturated NaCl solution and then dried with $MgSO_4$, filtered and evaporated. The residue was purified with column chromatography over silica gel. $CHCl_3$:Methanol (9:1) was initially used as solvent, followed by a mixture of 2.5% $NH_4OH$ in methanol and $CHCl_3$.

In Another Example, the Preparation of TR-MLys is Provided:

1st Step: Synthesis of Lysine Methylester*HCl (MLys*HCl)

Lysine (Lys, 3 mmol) and TMSCl (trimethylsilyl chloride, 2 equivalents, 6 mmol) were stirred in MeOH (10 mL) at room temperature for 24 hours. The solvent was evaporated under reduced pressure and the crude white powder was used in the 3rd step with TR-NHS without further purifications. MLys*HCl is analyzed by $^1$H NMR and $^{13}$C NMR.

2nd Step: Synthesis of TR-NHS 10,12 tricosadiynoic acid (TR) (1 eq, 0.289 mmol, 100 mg) was solubilized in $CH_2Cl_2$ (3 mL) in a round bottom flask under a gentle flux of $N_2$ and avoiding light contact (wrapping the flask with an aluminum foil). 1.2 eq of NHS (0.346 mmol, 40 mg) and EDC (2 eq, 0.547 mmol) were solubilized in $CH_2Cl_2$ and mixed with TR under stirring. After 18 hours, the solvent was evaporated at room temperature. The mixture was extracted from water with diethylether (×2, 100 mL). The organic layer was recovered, dried with anhydrous $NaSO_4$, filtered and evaporated. TR-NHS was used in the next step without further purification.

TR-NHS was analyzed by $^1H$ NMR and $^{13}C$ NMR.

3rd Step: Synthesis of TR-MLys

TR-NHS crude (from 2nd step) (0.243 mmol) was solubilized in $CH_2Cl_2$ in a round bottom flask under a gentle flux of $N_2$ and avoiding light contact. MLys*HCl (1.5 eq., 0.487 mmol) was added to the mixture followed by dropwise addition of triethylamine (1.2 eq, 0.292 mmol). The reaction was stirred at room temperature for 24 hours. After checking in TLC (thin layer chromatography), the mixture is purified with column chromatography (ethylacetate:cyclohexane=gradient elution) to yield the product as a white film. The solvent was removed under a gentle flux of an inert gas.

TR-MLys was analyzed by $^1H$ NMR and $^{13}C$ NMR, stocked at $-20°$ C.

Preparation of PDAs Having an Alcoholic Head Group

N-(2-ethanol)docosa-10,12-diynamide (TR-OH) was prepared in a similar manner by a collaborative laboratory.

Preparation of PDAs Having an Aliphatic Head Group 2-(docosa-10,12-diynamido)-4-methylpentanoic acid (TR-Leu) and methyl-2-(docosa-10,12-diynamide)-4-methylpentanoate (TR-MLeu) were prepared in a similar manner by a collaborative laboratory.

Preparation of PDAs Having an Aromatic Head Group 2-(docosa-10,12-diynamido)-3-phenylpropanoic acid (TR-Phe or TR-phA), methyl 2-(docosa-10,12-diynamido)-3-phenylpropanoate (TR-MPhe or TR-MphA) and (4-(docosa-10,12-diynoloxy)phenyl)boronic acid (TR-PhB) were prepared in a collaborative laboratory.

In One Example, the Preparation of TR-MPh is Provided:

$1^{st}$ Step: Synthesis of Phenylalanine Methylester*HCl (MPhe*HCl)

Phenylalanine (Phe, 3 mmol, 496 mg) and TMSCl (trimethylsilyl chloride, 2 eq., 6 mmol) were stirred in MeOH (10 mL) at room temperature for 24 hours. The solvent was evaporated under reduced pressure and the crude (white powder) was used in the 3rd step with TR-NHS without further purifications. MPhe*HCl was analyzed by 1H-NMR and 13C-NMR.

2nd Step: Synthesis of TR-NHS 10,12 tricosadiynoic acid (TR) (1 eq, 0.289 mmol, 100 mg) was solubilized in $CH_2Cl_2$ (3 mL) in a round bottom flask under a gentle flux of $N^2$ avoiding light contact (wrapping the flask with an aluminum foil). 1.2 eq of NHS (0.346 mmol, 40 mg) and EDC (2 eq, 0.547 mmol) were solubilized in $CH_2Cl_2$ and mixed with TR under stirring. After 20 hours, the solvent was evaporated at room temperature. The mixture was extracted from water with diethylether (×2, 100 mL). The organic layer was recovered, dried with anhydrous NaSOwa, filtered and evaporated. TR-NHS was used in the next step without further purification. TR-NHS was analyzed by 1H-NMR and 13C-NMR.

$3^{rd}$ Step: Synthesis of TR-MPhe

TR-NHS crude (2nd step) (0.243 mmol) was solubilized in $CH_2Cl_2$ in a round bottom flask under a gentle flux of N2 and avoiding light contact (wrapping the flask with an aluminum foil). MPhe*HCl (2 eq., 0.487 mmol) was added to the mixture followed by dropwise addition of triethylamine (1.2 eq, 0.292 mmol). The reaction was stirred at room temperature for 24 hours. After checking in TLC (thin layer chromatography), the mixture was purified with column chromatography (ethylacetate:cyclohexane=1:5 to 1:2 gradient elution) to yield the product as a white film. The solvent was removed under a gentle flux of an inert gas.

TR-MPhe was analyzed by 1H-NMR and 13C-NMR, stocked at $-20°$ C., it was stored wrapped with an aluminum foil to avoid the formation of blue impurities.

In Another Example, the Preparation of TR-NaPh is Provided:

1st Step—Synthesis of Tricosa-10,12-Diynoyl Chloride (TR-Cl)

Oxalylchloride (1.2 eq, 1.68 mmol) was added dropwise to a $CH_2Cl_2$ (15 mL) stirring solution containing 1 (1 eq, 1.40 mmol). The resulting mixture was stirred for 3 hours at RT. Removal of the solvent under reduced pressure afforded the desired TR-Cl in quantitative yield and the product was used for the next reaction without further purification. Yield: oily liquid (97%).

2nd Step—Synthesis of Naphthalen-2-Yl Tricosa-10,12-Diynoate (TR-Naph, 2).

To a stirring solution of TR-Cl (1 eq, 0.30 mmol) in $CH_2Cl_2$ (15 mL) was added 2-naphtol (2 eq, 0.60 mmol) and $Et_3N$ (3 eq, 0.36 mmol); the resulting solution was stirred at RT overnight, avoiding light contact. The mixture was extracted from water with $CH_2Cl_2$ (×2, 50 mL). The organic layers were recovered, dried with anhydrous Na2SO4 and filtered. Evaporation of the solvent left a white solid, that was purified by column chromatography (AcOEt: cyclohexane=1:9). Yield: white solid (95%).

Preparation of PDAs Having a Fluoro Head Group 2,2,2-trifluoroethyl docosa-10,12-diynoate (TR-F3 or TR-Flu), 3,3,4,4,5,5,6,6,7,7,8,8,9,9,10,10-heptadecafluorodecyl docosa-10,12-diynoate (TR-F10) and 1,1,1,3,3,3-hexafluoropropan-2-yl docosa-10,12-diynoate (TR-iF6) were prepared by conventional chemistry by a collaborative laboratory.

Example 2

Preparation of PDA Films on PMMA

PDA layers [and/or PDA derivatives] can be deposited on PMMA planar surfaces or on PMMA beads having different diameters. While the following examples are provided for PMMA planar surfaces, the deposition on beads is carried out through a similar protocol.

PDA Having Small Hydrophilic Head Groups (Carboxylic and Amine) Films on PDDA

FIG. 1A depicts an experimental scheme for spin coating two different PDA head groups (carboxylic and amine) on PMMA, and the resultant film morphology.

The diacetylene monomers, such as 10,12-tricosadiynoic acid and 10,12-tricosadiyn amine, were dissolved in a solvent comprising THF and DCM at a 1:1 mole ratio in a concentration of 45 mg/mL. The solution was filtered through a membrane filter (Millex, Nylon, 0.45 µm). The PMMA substrates were cut into circular plates of 1 cm diameter. 40 µL of the monomer was dropped onto the PMMA and after 30-50 seconds were spin-coated at 2500 rpm for 30 seconds.

In the case of the diacetylene mixture of carboxylic derivative and amine derivative, 10,12-tricosadiyn amine (TR-EDA) was mixed with 10,12-tricosadiynoic acid at a mole ratio of 1:9 and the rest of the procedure was similar to the above procedure for pure 10,12-tricosadiynoic acid.

The same procedure was repeated for diacetylene monomers comprising other amine head groups, at various ratios 1:1, 1:3, 2:3, 1:6, and 1:9.

PDA/TR-F3, PDA/TR-F10 and PDA/TR-iF6 Films on PDDA

As an example, TRCDA/TR-F3 solutions were prepared in the mole ratio 2:3 in THF/DCM solution mixture of equal volume.

The spin-coated films were irradiated with ultraviolet light (254 nm) for 0.3 to 1 minutes to produce the polymerized, blue phase of polydiacetylene.

Films were prepared at various ratios 1:1, 1:3, 2:3, 1:6, and 1:9 as compared to the monomer having a small hydrophilic head group (here TRCDA).

Phosphatidylethanoleamine (PE)/PDA Films on PMMA Surface

Mixed films of PDA [or PDA derivatives] and phospholipids, or other surfactants can also be made. For example, phosphatidylethanoleamine (PE) and PDA were used in a molar ratio of 2:3 in a solvent mixture comprising of THF: DCM of equal volume. 40 µL of solution was taken and dropped to a clean PMMA Perspex. After waiting for 30 seconds, the spin coating was done at 1500 rpm for 30 seconds, to get PE/PDA film over PMMA Perspex.

The PDA films thus obtained were UV irradiated for 0.3 minutes to get blue color.

Films were prepared at various ratios 1:1, 1:3, 2:3, 1:6, and 1:9 as compared to the monomer having a small hydrophilic head group (here TRCDA).

PDA/Monensin Films on PMMA Surface

PDA and Monensin were used in the molar ratio of 2:1 in a solvent mixture of THF:DCM of equal volume and spin coated over PMMA at 1500 rpm for 30 seconds.

PE/PDA/Monensin Films on PMMA Surface

PE, PDA and Monensin were used in the molar ratio of 2:3:1, dissolved in a solvent mixture of THF:DCM of equal volume and spin coated over PMMA at 1500 rpm for 30 seconds.

PDA/TTA, PDA/BTOT and PDA-TEA/BTOT Films on a PMMA Surface

Experiments were conducted with PDA matrices comprising different combinations of PDA, TTA, and BTOT.

The diacetylene monomers (10,12-tricosadiynoic acid (TRCDA) and N-(2-aminoethyl)tricosa-10,12-diynamide (TEA)), the organic ligands thenoyltrifluoroacetone (TTA) and BTOT, as well as polyvinylpyrrolidone (PVP), were dissolved in chloroform (50 mg/mL). The solutions of diacetylene monomers were filtered through a membrane filter (Millex, Nylon, 0.45 µm). For diacetylene mixtures, mixtures of 50% regular TRCDA and 50% derivative, were used. For example: TRCDA/PVP (mole ratio, 2/1), TRCDA/TTA/PVP (2/1/1), TRCDA/BTOT/PVP (2/1/1) and TEA/BTOT/PVP (2/1/1) were prepared for the following spin-coating procedure. The PMMA substrates were cut into circular plates of 1 cm diameter.

Preparation of PDA/TR-MPhe, PDA/TR-PHE and PDA/TR-PhB Films on a PMMA Surface:

A Control solution was prepared by mixing TFE (30 l), distillate water (270 L) and 40 mM Tris buffer (300 L, at pH=8.0).

A Red Control was prepared by coating a disk with PDA/PDA-derivative that had already been polymerized and warming it at an oven at 70° C. until the film changed its color to Red.

The PDA/TR-MPhe, PDA/TR-PHE and PDA/TR-PhB films were prepared as described hereinabove.

Example 3

Application of PDA and PDA-Amine/PMMA for Detection of SCC in Milk 6 samples of milk were provided from infected cows, at different cell concentrations, as well as from uninfected cows, and were incubated with unmodified PDA/PDA-$NH_2$/PMMA at two PDA/Amine-PDA mole ratios: 8:2 (20% PDA-Amine) and 9:1 (10% PDA-Amine), on coated perspex circles for 3 hours at room temperature.

Color changes of PDA/amine-PDA/PMMA substrates treated with milk taken from both infected and non-infected cows, were recorded as a function of time (not provided). The results clearly show the formation of red patches of color after 30 minutes from placing the samples on the films, for samples taken from cows infected, as compared to the original color of the PDA/PDA-amine/PMMA substrate at time zero. In contrast, the color of the substrate treated by milk of un-infected cows, had hardly changed color.

Color changes over time of two different PDA/amine-PDA mole ratios (8:2, 9:1) of PDA/PMMA substrate, treated with milk of infected cows at different SCC concentrations, were recorded (not provided), whereas 1 denotes 38,000 cells/mL ("un-infected cow" control), 2 denotes 560,000 cells/mL, 3 denotes 1,900,000 cells/mL, 4 denotes 2,000,000 cells/mL, 5 denotes 4,700,000 cells/mL, 6 denotes 7,000,000 cells/Ml.

Figure 11:
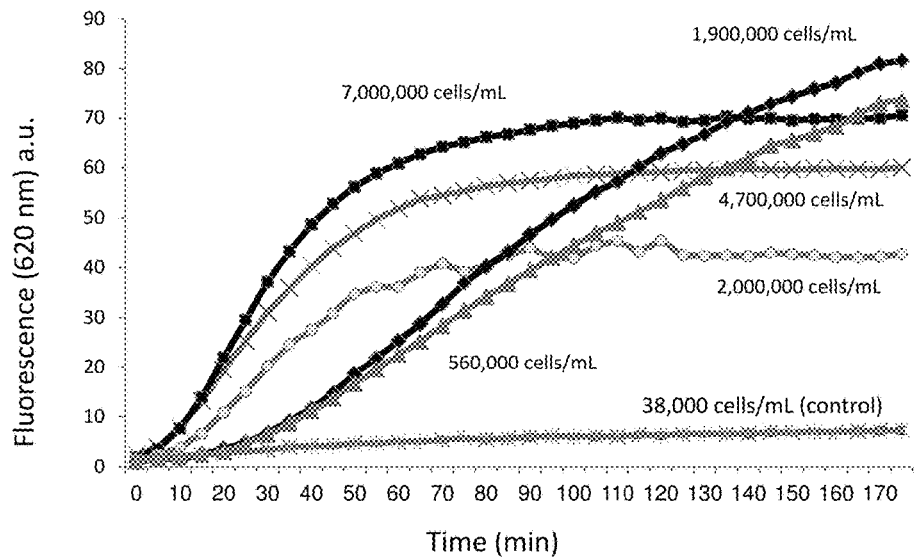
FIGS. 11 and 12 are fluorescent curves, corresponding to the intensity of the fluorescence peak at 620 nm. Both figures show that within 30 minutes the polymer substrate can discriminate between different SCC cells.
Figure 12:
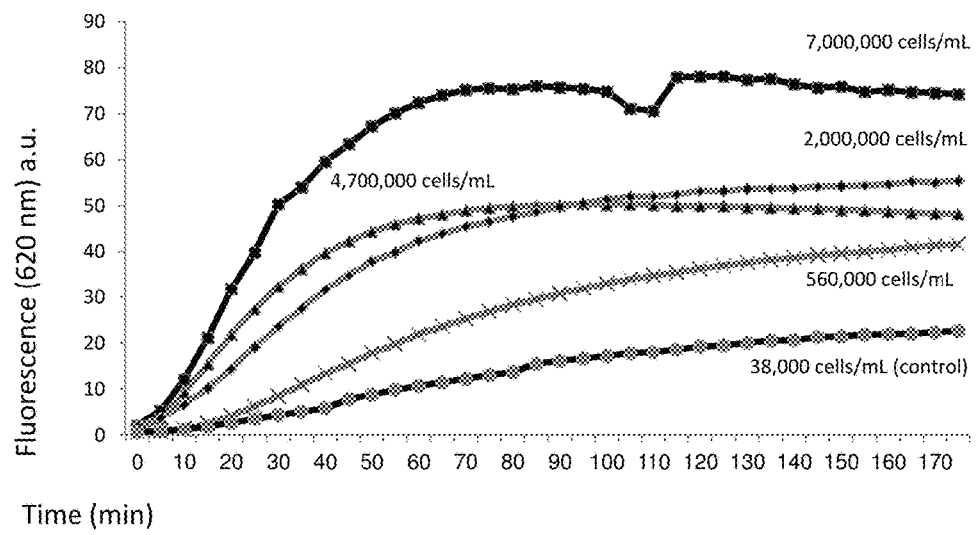

Another experiment measured the rate of increase in fluorescence of the polymer substrate in contact with milk. The fluorescence of milk samples contacted with 'formulation 1' (8:2 PDA:amine-PDA/PMMA film) and with 'formulation 2' (9:1 PDA:amine-PDA/PMMA film) are presented in FIGS. 12 and 11, respectively. FIGS. 11 and 12 are fluorescent curves, corresponding to the intensity of the fluorescence peak at 620 nm. Both figures show that within 30 minutes the polymer substrate can discriminate between different SCC cells.

FIGS. 15A-C represent fluorescent spectrum of the blue film (before addition of milk, or upon addition of the control milk) and red film.

Example 4

Application of PDA-Amine/PMMA for Detection of Bacteria

Figure 13:
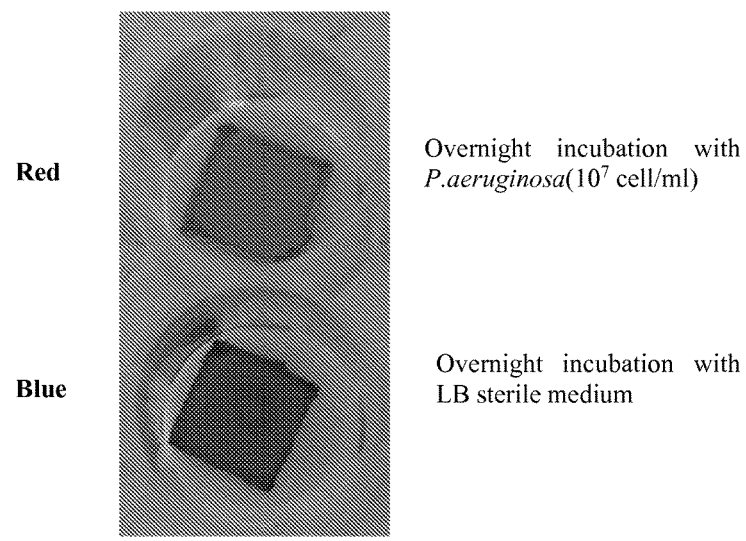
FIG. 13 shows that PDA/PMMA film placed in the bacterial suspension undergoes a blue-red color transition.

PDA-amine was spin-coated upon the PMMA surface. Following UV polymerization, the films were incubated within a solution of *P. auruginosa* ($10^7$ cells/mL in a LB growth medium) as well as a control solution containing only LB. After incubation, the PDA/PMMA film placed in the bacterial suspension started to undergo a blue-red color transition. The color change started within 1 hour, and a complete blue-red change was apparent after 12 hours, as can be seen in FIG. 13. The control LB solution induced minimal color transition (blue-purple).

Example 5

Application of PDA and PDA-Amine/PMMA for Detection of Surfactants in Water Surfactant-Induced Color Change. The tested amphiphilic compounds were first dissolved in the solvent 2,2,2-trifluroethanol and the solution was diluted to a final concentration of 1 mM by mixing with Trizmabase® buffer at pH 8. Polymerized PMMA-coated PDA films were placed in 48-well plates. 300 μL of surfactant solutions (1 mM) were added on top of the PDA-PMMA films and the chromatic changes were recorded.

The color changes of the PDA/PMMA films can be quantified through application of a simple image analysis algorithm (Pevzner et al., 2008) providing the means for both comparing the different colors induced, as well as evaluating the time-dependent colorimetric transformations (FIGS. 3A and 3B) FIGS. 3A and 3B disclose time-dependent % RGB curves reflecting the extent of blue-red-yellow transformation of the PDA/PMMA film (A) and PDA-NH$_2$/PDA/PMMA film (B) after addition of amphiphilic compounds 1-10.

FIGS. 4A-4D disclose spectroscopic characterization of PMMA-supported PDA films undergoing distinct color transitions. The four compounds shown represent different color transitions: CTAB (yellow); C12mimCl (red); triton X-100 (purple); SDBS (magenta). (A) UV-vis absorbance spectra of PDA/PMMA; (B) UV-vis absorbance spectra of PDA-NH$_2$/PDA/PMMA; (C) fluorescence emission spectra of PDA/PMMA, excitation: 482 nm; (D) Fluorescence emission spectra of PDA-NH$_2$/PDA/PMMA, excitation: 482 nm.

Example 6

Application of PE/PDA/PMMA, PDA/Monensin/PMMA and PE/PDA/Monensin/PMMA for the Detection of Ions in Water, in the Presence of Ionophores 100 mM and 50 mM solutions of Sodium (NaCl) and Potassium (KCl) ions were prepared in Tris Buffer of pH 8. UV irradiated PDA, PE/PDA, PDA/Monensin and PE/PDA/Monensin substrates were placed inside well plates. Na+, K+, Li+, Ba+2, Cu+2 solutions were added over the Perspex in each well and color changes were observed.

After 2 hours of scanning, the well plates were placed in a plate reader (varioscan) and absorption and emission spectra (480 nm excitation) were measured.

After preparing the films solutions with different concentrations of metal cations were added and the chromatic response was monitored. The color changes of PDA and PDA-Monensin were recorded 2 hours after the addition of different ions. The results can be seen in FIG. 6.

Films were prepared at various ratios 1:1, 1:3, 2:3, 1:6, and 1:9.

Example 7

Application of PDA/TTA/PMMA, PDA/BTOT/PMMA and PDA-TEA/BTOT/PMMA for the Detection of Lanthanides in Water The tested lanthanide salts were first dissolved in Trizmabase buffer at pH=8.0 at a concentration of 1 mM. Polymerized PMMA-coated PDA films were placed in 48-well plates. Three hundred microliters of lanthanide solutions (1 mM) were added on top of the PDA-PMMA films and the chromatic changes were recorded with an incubation time of 10 minutes.

The color changes of PDA and PDA/chelator films spin-coated upon a transparent Perspex substrate (including incorporation of an amine-displaying polydiacetylene denoted PDA-TEA, designed to increase sensitivity and specificity upon binding to the positive headgroup), were quantified using a simple algorithm utilizing the scanned images (FIG. 14).

Example 8

Application of PDA/Modified PDAs/PMMA for Fingerprinting Detection of Oils in Water Experiments were conducted using detector systems comprising PDA/modified PDA (with different derivatives of PDA, as listed in Table 1), showing different chromatic responses for PDA systems comprising 50% unmodified PDA and 50% of different PDA derivatives, according to the "fingerprint concept.

Mastic (triterpenic resin), Gum Karaya (Polysaccharide) and Fish glue (Glues mainly Collagen) were dissolved in TFE (10 mg/mL).

20 μL from this mother solution were taken and dissolved in 300 μL of Tris buffer at pH-8.

Colorimetric scanning was done for 1 hour and absorbance and fluorescence spectra were checked with the plate reader.

The color change of PDA, PDA/NH$_2$ and PDA/F3 were recorded at 0, 3, 10, 20, 30, 40, 50 and 60 minutes after the addition of gums. The results can be seen in FIGS. 7-10.

Example 9

Application of PDA/TR-Lys/PMMA and PDA/TR-MPhe/PMMA and Other PDAs for Detection of Pesticides in Water Sonication of 4 mL vials with the mixed solutions of OP+ buffer was conducted for 1-2 minutes. The vial was vortexed for a few seconds at the lowest possible speed, and the mixed solution (300 μL) was immediately transferred into the appropriate well over the PDA/PDA derivatives coated Perspex. Special care should be taken to ensure that the Perspex is not partly floating in the solution and bubbles are to be removed if necessary. The order of addition should be preserved in the following experiments according to the different OP. A "control" sample containing TFE and Tris buffer at a molar ratio of 1:20 should be added last in the order of addition.

The 48 well plate were incubated for 90 minutes in the incubator at 27.0° C.-28.0° C. Then fluorometric scanning was performed.

Results of different PDA derivatives for several organophosphate pesticides are provided in FIGS. 15A-15C (FIG. 15A: PDA/TR-NaPh 1:1; FIG. 15B: PDA/TR-DEA; FIG. 15C: PDA/TR-MPhe).

Films were prepared at various ratios 1:1, 1:3, 2:3, 1:6, and 1:9 as compared to the monomer having a small hydrophilic head group (here TRCDA).

While specific embodiments of the invention have been described for the purpose of illustration, it will be understood that the invention may be carried out in practice by skilled persons with many modifications, variations and adaptations, without departing from its spirit or exceeding the scope of the claims.

The invention claimed is:

1. A colorimetric and/or fluorescent detector, which comprises a polydiacetylene (PDA) film deposited on a polymethylmetacrylate (PMMA) substrate, wherein said colorimetric and/or fluorescent detector is a solid organic matrix comprising one or more polydiacetylenes (PDA) deposited on said polymethylmetacrylate (PMMA) substrate, wherein said PDA comprises polymerized units of diacetylene monomers, wherein at least a portion of said diacetylene monomers have a hydrophilic head group serving as a recognition element, said hydrophilic head group is selected from the group consisting of an amine group, hydroxyl group, amide group, phosphate group, boronic acid group, halogen group and ammonium salt group.

2. The colorimetric and/or fluorescent detector of claim 1, wherein said hydrophilic head group is an amine group covalently bound to the diacetylene monomer.

3. The colorimetric and/or fluorescent detector of claim 2, wherein said diacetylene monomer having an amine group is selected from the group consisting of 10,12-tricosadiyn amine, N-(2-aminoethyl)docosa-10,12-diynamide, 2-(docosa-10,12-diynamido)-N,N,N-trimethylethanaminium, methyl 6-amino-2-(docosa-10, 12-diynamido)hexanoate.

4. The colorimetric and/or fluorescent detector of claim 1, wherein said hydrophilic head group is a halogen group covalently bound to the diacetylene monomer.

5. The colorimetric and/or fluorescent detector of claim 4, wherein said halogen group is a fluoro group and the diacetylene monomer is selected from the group consisting of 2,2,2-trifluoroethyl docosa-10,12-diynoate, 3,3,4,4,5,5,6, 6,7,7,8,8,9,9,10,10-heptadecafluorodecyl docosa-10,12-diynoate, 1,1,1,3,3,3-hexafluoropropan-2-yl docosa-10,12-diynoate.

6. The colorimetric and/or fluorescent detector of claim 1, wherein said hydrophilic head group is a hydroxy group covalently bound to the diacetylene monomer.

7. The colorimetric and/or fluorescent detector of claim 1, wherein the at least a portion of diacetylene monomers is between 40 molar percent to 90 molar percent.

8. The colorimetric and/or fluorescent detector of claim 1, wherein said diacetylene monomers are selected from: 2-(docosa-10,12-diynamido)-3-phenylpropanoic acid, methyl 2-(docosa-10,12-diynamido)-3-phenylpropanoate, (4-(docosa-10,12-diynoloxy)phenyl)boronic acid, 2,2,2-trifluoroethyl docosa-10,12-diynoate, 3,3,4,4,5,5,6,6,7,7,8,8,9, 9,10,10-heptadecafluorodecyl docosa-10,12-diynoate, 1,1,1, 3,3,3-hexafluoropropan-2-yl docosa-10,12-diynoate, 2-(docosa-10,12-diynamido)-4-methylpentanoic acid, and methyl-2-(docosa-10,12-diynamide)-4-methylpentanoate.

9. The colorimetric and/or fluorescent detector of claim 1, said detector further comprising a recognition element being an ionophore.

10. The colorimetric and/or fluorescent detector of claim 1, said detector further comprising a recognition element being a chelator.

11. The colorimetric and/or fluorescent detector of claim 2, wherein the at least a portion of diacetylene monomers is between 40 molar percent to 90 molar percent.

12. The colorimetric and/or fluorescent detector of any claim 3, wherein the at least a portion of diacetylene monomers is between 40 molar percent to 90 molar percent.

13. The colorimetric and/or fluorescent detector of claim 4, wherein the at least a portion of diacetylene monomers is between 40 molar percent to 90 molar percent.

14. The colorimetric and/or fluorescent detector of claim 5, wherein the at least a portion of diacetylene monomers is between 40 molar percent to 90 molar percent.

15. The colorimetric and/or fluorescent detector of claim 6, wherein the at least a portion of diacetylene monomers is between 40 molar percent to 90 molar percent.

* * * * *